(12) United States Patent
Yokomizo et al.

(10) Patent No.: US 7,429,469 B2
(45) Date of Patent: Sep. 30, 2008

(54) ENZYME GENE PARTICIPATING IN THE SYNTHESIS OF POLYESTER AND PROCESS FOR PRODUCING POLYESTER USING THE SAME

(75) Inventors: Satoru Yokomizo, Kobe (JP); Takeshi Fukuchi, Akashi (JP); Fumio Osakada, Okayama (JP); Keiji Matsumoto, Nishinomiya (JP); Masamichi Takagi, Fuchu-shii (JP); Akinori Ohta, Saitama (JP)

(73) Assignee: Kaneka Corporation, Osaka (JP)

( * ) Notice: Subject to any disclaimer, the term of this patent is extended or adjusted under 35 U.S.C. 154(b) by 504 days.

(21) Appl. No.: 10/491,498

(22) PCT Filed: Oct. 9, 2002

(86) PCT No.: PCT/JP02/10461

§ 371 (c)(1),
(2), (4) Date: Aug. 10, 2004

(87) PCT Pub. No.: WO03/033707

PCT Pub. Date: Apr. 24, 2003

(65) Prior Publication Data

US 2007/0020739 A1 Jan. 25, 2007

(30) Foreign Application Priority Data

Oct. 10, 2001 (JP) ............................ 2001-312178

(51) Int. Cl.
*C07H 21/04* (2006.01)
*C12P 7/62* (2006.01)
*C12N 15/74* (2006.01)
*C12N 1/21* (2006.01)

(52) U.S. Cl. .................... 435/135; 435/254.2; 435/483; 435/254.21; 435/254.22; 435/254.23; 536/23.2

(58) Field of Classification Search ........................ None
See application file for complete search history.

(56) References Cited

FOREIGN PATENT DOCUMENTS

| EP | 0 824 148 A2 | 2/1998 |
|---|---|---|
| JP | 57-150393 | 7/1983 |
| JP | 59-220192 | 7/1984 |
| JP | 5-93049 | 3/1993 |
| JP | 7-265065 | 10/1995 |
| JP | 10-108682 | 2/1998 |
| JP | 2002-262886 | 12/2003 |
| WO | WO 9935278 | * 7/1999 |
| WO | WO 00/43525 | 7/2000 |
| WO | WO 01/88144 | 11/2001 |

OTHER PUBLICATIONS

Fukui et al. J. Bactrol. 1997, pp. 4821-4830.*

T. Fukui et al., "Cloning and Analysis of the Poly (3-Hydroxybutyrate-co-3-Hydroxyhexanoate) Biosynthesis Genes of Aeromonas caviae", Journal of Bacteriology, 179(15):4821-4830 (1997).
E. H. Hettema et al., "Import of proteins into peroxisomes", Biochimica et Biophysica Acta, 1451:17-34 (1999).
K. Kondo, "Kobo Candida utilis no Ishu Idenshi Hatsugenkei", Kagaku to Seibutsu, 38(9):614-620 (2000) with summary in English.
T. A. Leaf et al., "Saccharomyces cerevisiae expressing bacterial polyhydroxybutyrate synthase produces poly-3-hydroxybutyrate", Microbiology, 142:1169-1180 (1996).
V. Mittendorft et al., "Synthesis of medium-chain-length polyhydroxyalkanoates in Arabidopsis thaliana using intermediates of peroxisomal fatty aicd β-oxidation", Proc. Natl. Acad. Sci, USA, 95:13397-13402 (1998).
Y. Poirier et al., "Synthesis of Polyhydroxyalkanoate in the Peroxisome of Saccharomyces cerevisiae by Using Intermediates of Fatty Acid β-Oxidation", Applied and Environmental Microbiology, 67(11):5254-5260 (2001).
Q. Ren, et al., "FabG, and NADPH-Dependent 3-Ketoacyl Reductase of Pseudomonas aeruginosa, Provides Precursors for Medium-Chain-Length Poly-3-Hydroxyalkanoate Biosynthesis in Escherichia coli", Journal of Bacteriology, 182(10):2978-2981 (2000).
Sequence Listing from WO 01/88144 A3 (XP-002377462).
Sequence Listing from WO 01/88144 A4 (XP-002377463).
Sequence Listing from Fukui, T., et al., "Cloning and Analysis of the Poly(3-Hydroxyalkanoate-Co-3-Hydroxyalkanoate) Biosynthesis Genes of Aeromonas Caviae", Journal of Bacteriology, vol. 179, No. 15, Aug. 1997, pp. 4821-4830. (XP-002377464).
Fukui, T., et al., "Co-Expression of Polyhydroxyalkanoate Synthase and (R)-Enoyl-Coa Hydratase Genes of Aeromonas Caviae Establishes Copolyester Biosynthesis Pathway in Escherichia coli", FEMS Microbiology Letters, vol. 170, 1999, pp. 69-75.
Subramani, Suresh, "Protein Import into Peroxisomes and Biogenesis of the Organelle", Annual Review of Cell Biology, vol. 1993, pp. 445-478.
Allenbach, Laure, et al., "Analysis of the Alternative Pathways for the β-Oxidation of Unsaturated Fatty Acids Using Transgenic Plants Synthesizing Polyhydroxyalkanoates in Peroxisomes", Plant Physiology, vol. 124, No. 3, Nov. 2000, pp. 1159-1168.
Miura, Y., et al., "Production of the Carotenoids Lycopene, β-Carotene, and Astaxanthin in the Food Yeast Candida utilis", Applied and Environmental Microbiology, Apr. 1998, vol. 64, No. 4, pp. 1226-1229.

* cited by examiner

Primary Examiner—Rebecca E. Prouty
Assistant Examiner—Mohammad Younus Meah
(74) Attorney, Agent, or Firm—Kenyon & Kenyon LLP

(57) ABSTRACT

This invention relates to a method of producing polyesters resulting from homopolymerization or copolymerization of a 3-hydroxyalkanoic acid(s) and having biodegradability and good physical properties using yeasts as hosts. By constructing at least one enzyme gene involved in polyester synthesis by adding a DNA coding a peroxisome-targeting signal, introducing an enzyme gene expression cassette containing that gene into yeast, and cultivating the thus-obtained transformant, it becomes possible to cause accumulation of a polyester resulting from homopolymerization or copolymerization of a 3-hydroxyalkanoic acid(s) in yeast cells and recover the polyester from the culture.

15 Claims, 12 Drawing Sheets

ENZYME GENE PARTICIPATING IN THE SYNTHESIS OF POLYESTER AND PROCESS FOR PRODUCING POLYESTER USING THE SAME

This application is a 371 national phase application of PCT/PJ02/10461 filed on 09 Oct. 2002, claiming priority to JP 2001-312178, filed on 10 Oct. 2001, the contents of which are incorporated herein by reference in their entirety.

TECHNICAL FIELD

The present invention relates to genes necessary for the enzymatic synthesis of polyesters, a microorganism fermentatively synthesizing polyesters utilizing the gene, and a method of producing polyesters using the microorganism. More particularly, it relates to genes capable of functioning in a host enzymatically synthesizing plastic-like polymers decomposable under the action of microorganisms in the natural environment (in soil, rivers and seas), a transformant resulting from transformation with the gene and improved in the capacity to fermentatively synthesize plastic-like polymers, and a method of producing polyesters utilizing the transformant.

BACKGROUND ART

At present, a large number of microorganisms are known to store polyester as an energy source substance within cells. A typical example of the polyester is poly-3-hydroxybutyric acid (hereinafter referred to briefly as P(3HB)), which is a homopolymer of 3-hydroxybutyric acid (hereinafter referred to as 3HB for short). It was first discovered in *Bacillus megaterium* (M. Lemoigne, Ann. Inst. Pasteur, 39, 144 (1925)). P(3BH) is a thermoplastic polymer and is biodegradable in the natural environment and, thus, has recently attracted attention as an ecofriendly plastic. However, P(3HB) is high in crystallinity, and hard and fragile by nature, so that the range of practical application thereof is limited. Therefore, studies have been undertaken to modify the same for bringing about improvements in these properties.

In Japanese Kokai Publication Sho-57-150393 and Japanese Kokai Publication Sho-59-220192, among others, a technology of producing a copolymer made of 3-hydroxybutyric acid (3HB) and 3-hydroxyvaleric acid (3HV) (hereinafter such copolymer is referred to as P(3HB-co-3HV)) is disclosed. This P(3HB-co-3HV) is rich in flexibility as compared with P(3HB), hence was considered to have a wide application range. In actuality, however, P(3HB-co-3HV) shows only slight changes in physical properties even when the mole fraction of 3HV is increased. In particular, the flexibility, which is required for its use in films and the like, will not be improved. Thus, it has been used only in the field of rigid shaped articles such as shampoo bottles and disposable razor grips.

In recent years, studies have been made concerning copolyesters consisting of two components 3HB and 3-hydroxyhexanoic acid (hereinafter referred to as 3HH for short) (hereinafter such copolyesters are referred to as P(3HB-co-3HH) for short), as described in Japanese Kokai Publication Hei-05-93049 and Japanese Kokai Publication Hei-07-265065, among others. According to these publications, this technology of producing P(3HB-co-3HH) comprises fermentative production thereof from a fatty acid, such as oleic acid, or an oil or fat, such as olive oil, using *Aeromonas caviae* isolated from soil. Studies concerning the properties of P(3HB-co-3HH) have also been made (Y. Doi, S. Kitamura, H. Abe, Macromolecules, 28, 4822-4823 (1995)). According to this report, when *A. caviae* is cultured using a fatty acid containing not less than 12 carbon atoms as the only carbon source, P(3HB-co-3HH) with a 3HH content of 11 to 19 mole percent can be fermentatively produced. It has been revealed that the properties of such P(3HB-co-3HH) change from hard and brittle gradually to soft and flexible, to an extent exceeding the flexibility of P(3HB-co-3HV), with the increase in mole fraction of 3HH. However, the above method of production is low in productivity, namely the yield of cells is 4 g/L and the polymer content is 30%. Therefore, methods capable of attaining higher productivity for practical use have been searched for.

A PHA (polyhydroxyalkanoic acid) synthase gene has been cloned from *Aeromonas caviae*, which is a producer of P(3HB-co-3HH) (T. Fukui, Y. Doi, J. Bacteriol., vol. 179, No. 15, 4821-4830 (1997); Japanese Kokai Publication Hei-10-108682). This gene was transformed into *Ralstonia eutropha* (formerly *Alcaligenes eutrophus*), and cultivation was carried out using the resulting transformant and a vegetable oil as the carbon source, whereby a content in cells of 4 g/L and a polymer content of 80% were attained (T. Hukui et al., Appl. Microbiol. Biotechnol., 49, 333 (1998)). A method of producing P(3HB-co-3HH) using a bacterial species, such as *Escherichia coli*, or a plant as the host has also been disclosed (WO 00/43525), without describing any productivity data, however.

The above-mentioned polymer P(3HB-co-3HH) can be given a wide range of physical properties, from properties of rigid polymers to properties of flexible polymers, by changing the mole fraction of 3HH and therefore can be expected to be applicable in a wide range, from television boxes and the like, for which rigidity is required, to yarns, films and the like, for which flexibility is required. However, the production methods mentioned above are still poor in the productivity of P(3HB-co-3HH). There is no other way but to say that they are still unsatisfactory as production methods for the practical use of P(3HB-co-3HH).

In a recent study of the production of biodegradable polyesters, Leaf et al. used yeast high in cell productivity as the host (Microbiology, vol. 142, pp. 1169-1180 (1996)). Thus, the polyester synthase gene of *Ralstonia eutropha* was transformed into *Saccharomyces cerevisiae*, a kind of yeast, the thus-produced transformant was cultured using glucose as the carbon source, and the accumulation of P(3HB) was confirmed (polymer content 0.5%). However, the polymer produced in this study was that hard and brittle P(3HB).

Yeast is known to grow fast and be high in cell productivity. Among them, yeasts belonging to the genus *Candida* attracted attention as single cell proteins in the past and, since then, studies have been made on the production of cells thereof for use as feeds using normal-paraffins as carbon sources. Further, in recent years, vectors functioning in hosts belonging to the genus *Candida* have been developed, and the production of substances using the recombinant DNA technology has been reported (Kagaku to Seibutsu, vol. 38, No. 9, 614 (2000)). When *Candida utilis* is used as the host, the α-amylase productivity is as high as about 12.3 g/L. Microorganisms of the genus *Candida* having such high substance productivity are expected to serves as hosts in polymer production. Furthermore, cells thereof can be separated from the culture fluid with ease as compared with bacteria and, thus, the polymer extraction and purification steps can be facilitated.

Thus, the advent of a method of producing P(3HB-co-3HH) having good physical properties using yeast belonging to the genus *Candida* has been waited for.

SUMMARY OF THE INVENTION

In view of the above-mentioned state of the art, it is an object of the present invention to provide a gene involved in polyester synthesis which can be expressed in yeast in a functional and efficient manner, a yeast transformant transformed with a gene expression cassette comprising the gene, and a method of producing polyesters having biodegradability and good physical properties which comprises cultivating the transformant obtained in the above manner.

The present inventors made various investigations and, as a result, found that when novel genes, which are capable of being expressed in yeast, are produced by adding a peroxisome-targeting signal-encoding DNA to one or more genes each coding for an enzyme involved in polyester synthesis, a gene expression cassette is constructed by joining a promoter and terminator capable of substantially functioning in yeast to each of those genes, the resulting gene expression cassette is further transformed into yeast and the resulting transformant is cultivated, a polyester can be produced and recovered from the culture in such a manner that very high productivity can be expected.

Thus, the present invention relates to a gene capable of being expressed in yeast, which obtainable by addition of a DNA coding for a peroxisome-targeting signal to a gene coding for an enzyme involved in polyester synthesis.

In a preferred embodiment thereof, the invention relates to the gene as mentioned above herein the enzyme involved in polyester synthesis is a bacterial species-derived enzyme, more preferably from *Aeromonas caviae* and to the gene as mentioned above wherein at least one CTG codon in the gene coding for the bacterial species-derived enzyme has been modified into TTA, TTG, CTT, CTC or CTA.

In another preferred embodiment, the invention relates to a gene as mentioned above wherein the enzyme involved in polyester synthesis is a polyhydroxyalkanoic acid synthase or R-specific enoyl-CoA hydratase.

The present invention also relates to an enzyme involved in polyester synthesis, which is translated from the above gene.

The present invention further relates to a transformant resulting from transformation of at least one gene abovementioned into yeast. In a preferred embodiment, it relates to a transformant resulting from transformation, into yeast, of a polyester synthesis-associated enzyme gene expression cassette which comprises the above gene, a promoter and a terminator both capable of functioning in the yeast.

In another preferred embodiment, the invention relates to a transformant as defined above wherein the polyester is a homopolymer or copolymer of a 3-hydroxyalkanoic acid(s) represented by the general formula (1):

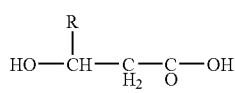

wherein R represents an alkyl group, and, more preferably to a transformant as defined above wherein the polyester is a copolyester, P(3HB-co-3HH), obtainable by represented by the formula (2):

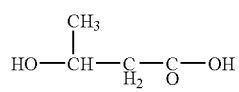

and 3-hydroxyhexanoic acid represented by the formula (3):

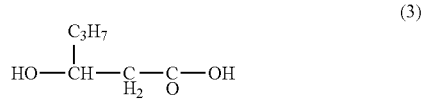

The present invention still further relates to a method of producing polyesters which comprises cultivating the above transformant and recovering a polyester from the culture obtained.

DETAILED DISCLOSURE OF THE INVENTION

In the following, the present invention is described in detail.

(1) Enzyme Involved in Polyester Synthesis and Gene Coding For Same

In the practice of the present invention, the polyester is not particularly restricted but preferably is a homopolymer or copolymer of a 3-hydroxyalkanoic acid(s) represented by the general formula (1):

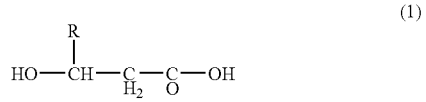

wherein R represents an alkyl group. Thus, preferred are a homopolymer of one 3-hydroxyalkanoic acid represented by the formula (1) or a copolymer of two or more 3-hydroxyalkanoic acids represented by the formula (1).

More preferred is a copolyester, P(3HB-co-3HH), represented by the formula (4):

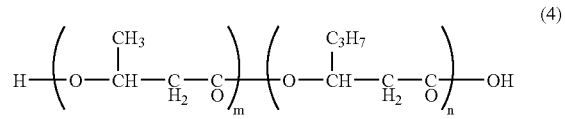

wherein m and n each represents an integer of not less than 1, as obtainable by copolymerization of 3-hydroxybutyric acid represented by the formula (2):

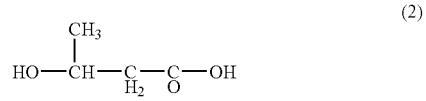

and 3-hydroxyhexanoic acid represented by the formula (3):

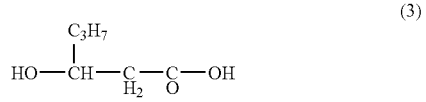

In the above general formula (1), R represents an alkyl group and preferably contains 1 to 11 carbon atoms, more preferably 1 to 4 carbon atoms, still more preferably 1 to 3 carbon atoms.

The "enzyme involved in polyester synthesis" so referred to herein includes not only polyester synthase but also polyester intermediate synthase. As the polyester synthase, there may be mentioned, among others, polyhydroxyalkanoic acid (hereinafter referred to as PHA) synthase. As the polyester intermediate synthase, there may be mentioned, among others, R-specific enoyl-CoA hydratase (T. Fukui, et al., FEMS Microbiology Letters, vol. 170, 69-75 (1999)) which converts enoyl-CoA, an intermediate in the β oxidation cycle, to an (R)-3-hydroxyacyl-CoA, which is a monomer, β-ketothiolase and NADPH-dependent acetoacetyl-CoA reductase (Peoples OP, et al., J. Biol. Chem., 264 (26), 15298-15303 (1989)) which dimerize acetyl-CoA and then reduce acetoacetyl-CoA to 3-hydroxybutyryl-CoA, which is a monomer, 3-ketoacyl-CoA reductase (fabG), (Qun Ren, et al., J. Bacteriol., vol. 182, No. 10, pp. 2978-2981), 3-hydroxyacyl-CoA epimerase (fadB), acyl-CoA dehydrogenase (Qun Ren, et al., Applied and Environmental Microbiology, Vol. 66, No. 4, pp. 1311-1320), etc.

Those enzymes involved in polyester synthesis are not particularly restricted but preferably are enzymes of bacterial origin, more preferably enzymes derived from *Aeromonas caviae* or *Ralstonia eutropha*. Thus, for example, enzymes described in Japanese Kokai Publication Hei-10-108682 can be used.

When yeast is transformed with a gene coding for such an enzyme of bacterial origin, the use of the bacterial gene as it is may lead to occurrence, in some host yeasts, of some abnormality in translation of genetic codons in some instances. For example, CTG codon is translated into serine, not into leucine, in the yeast *Candida cylindracea* (Y. Kawaguchi et al., Nature, 341, 164-166 (1989)) or *Candida maltosa* (H. Sugiyama et al., Yeast, 11, 43-52 (1995)). When a gene coding for an enzyme involved in polyester synthesis as derived from an organism other than yeasts is expressed in such a yeast, abnormality may occur in translation of a genetic codon, with the result that an enzyme differing in amino acid sequence from the desired enzyme may be produced. Thus, there is the possibility that the enzyme expressed cannot fully carry out the function of the desired enzyme.

Such problem can be solved by using a modified gene derived from the gene in question by converting CTG codon contained in the latter gene to another codon corresponding to leucine (TTA, TTG, CTT, CTC, or CTA) in advance. The leucine codon to be used in substitution for CTG is not restricted but, in view of the efficiency of translation of the gene to be transformed, it is preferably a genetic codon usage of which is high in the host yeast into which the gene is to be transformed. In *Candida maltosa*, for instance, it is desirable that CTG codon be converted to TTA or TTG, most preferably to TTG.

The codon usage constituting a gene varies from organism to organism. Thus, for amino acids other than tryptophan and methionine, there is a plurality of genetic codons corresponding to each amino acid but these differ in codon usage in an organism-dependent manner. In *Candida maltosa*, the genetic codons corresponding to alanine, for instance, are GCT, GCC, GCA and GCG and, among them, GCT is the genetic codon used most frequently in constituting a gene. In this way, which genetic codon is used among a plurality of genetic codons designating one and the same amino acid may differ from organism to organism. It has been pointed out that the efficiency of translation of a gene is high when the gene is composed of genetic codons with high codon usage. The GC contents of *Aeromonas caviae*-derived PHA synthase gene and R-specific enoyl-CoA hydratase gene, for instance, are 67.16% and 65.77%, respectively, whereas, for the *Candida maltosa*-derived enzymes so far reported, the GC content of phosphoglycerate kinase is 39.55% and the GC content of P450 (ALK2-A) is 35.67%.

Thus, the GC content in a gene varies as a result of the deviability of codon usage. Therefore, for attaining efficient expression of a gene involved in polyester synthesis in *Candida maltosa*, for instance, it is preferred that the relevant gene be modified not only by modification of CTG codon into another genetic codon corresponding to leucine, as mentioned above, but also by modification of some or other genetic codon (s) into one(s) with high codon usage in *Candida maltosa*.

Codon usage in *Candida maltosa* is described in Klaus Wolf (ed.): Nonconventional Yeasts in Biotechnology (published by Springer). Thus, GCT is preferred as the genetic codon for alanine, AGA for arginine, AAC or AAT for asparagine, GAT for aspartic acid, TGT for cysteine, GGT for glycine, CAA for glutamine, GAA for glutamic acid, CAC or CAT for histidine, ATT for isoleucine, TTG or TTA for leucine, AAA for lysine, TTC or TTT for phenylalanine, CCA for proline, TCT for serine, ACT for threonine, TAT or TAC for tyrosine, and GTT for valine. The genetic codons to be employed are not particularly restricted to these, however.

For example, when *Candida maltosa* is used as a host, the polyhydroxyalkanoic acid (PHA) synthase gene shown under SEQ ID NO:5, and the R-specific enoyl-CoA hydratase gene shown under SEQ ID NO:6 can be utilized as the genes for enzymes involved in polyester synthesis in the practice of the present invention.

As for the nucleotide sequences of these genes represented by SEQ ID NO:5 or 6, one or a plurality of nucleotides may have undergone mutation, such as deletion, substitution and/or addition, in their nucleotide sequences provided that they can provide substantial enzyme activities.

In this description, the expression "the nucleotide sequences in which one or a plurality of nucleotides may have undergone mutation, such as deletion, substitution and/or addition" means the nucleotide sequences with deletion, substitution, and/or addion, wherein the number of the nucleotide is in the extent of capable of being deleted, substituted, and/or added by the known method in the prior art, such as "Protein-Nucleic acid- Enzyme, a special issue, gene-amplifying PCR method TAKKAJ 35(17), 2951-3178(1990)", or "PCR technology(1990), edited by Henry A. Erlich, translated by Ikunoshin Kato", etc.

The DNA comprising the above nucleotide sequence may be the DNA capable of hybridizing with DNA, which comprises the nucleotide sequence of SEQ ID NO:5 or 6, in a stringent condition, provided that they can provide substantial enzyme activities.

"The DNA capable of hybridizing with DNA, which comprises the nucleotide sequence of SEQ ID NO:5 or 6, in a stringent condition" referred to herein means the DNA obtainable by colony hybridization method, plaque hybridization method, Southern hybridization method, among others, using a DNA comprising the nucleotide sequence of SEQ ID NO:5 or 6 as a probe. Those skilled in the art may easily obtain the desired DNA by carrying out said hybridization according to the method described in Molecular Cloning 2nd Edt. (Cold Spring Harbor Laboratory Press, 1989).

(2) Genes Capable of Being Expressed in Yeast, Added A DNA Coding For A Peroxisome Targeting Signal To A Gene Coding For An Enzyme Involved in Polyester Synthesis A characteristic feature of the present invention is that genes capable of being expressed in yeast, added a DNA coding for a peroxisome targeting signal to such a gene coding for an enzyme involved in polyester synthesis as mentioned above is utilized.

In fermentative production of a polyester using yeast, carbohydrates, fats and oils, fatty acids, n-paraffins and the like, which can be utilized by the yeast, can be used as the carbon sources, without any particular restriction. In fermentative polyester production using fats and oils, fatty acids, n-paraffins or the like as carbon sources, these carbon sources are metabolized via the β oxidation cycle, and the metabolic intermediates in the β oxidation cycle are utilized as substrates for polyester synthesis with good efficiency (T. Fukui, Y. Doi, J. Bacteriol., 179, No. 15, 4821-4830 (1997); Q. Ren et al., J. Bacteriol., 182, No. 10, 2978-2981 (2000)). Since the β oxidation in yeast is carried out in peroxisomes, which are intracellular microbodies, localization, in peroxisomes, of the enzyme(s) involved in polyester synthesis is favorable for efficient polyester synthesis.

The proteins to be transferred to peroxisomes are synthesized on free ribosomes and, owing to the function of a peroxisome-targeting signal occurring in the protein sequences, they are transferred to peroxisomes (S. Subramani, J. Membrane Biol., 125, 99-106 (1992); Y. Itai, Kagaku to Seibutsu 35, No. 10, 687-695 (1997); E. H. Hettema, Biochim. Biophys. Acta, 1451, 17-34 (1999)). Therefore, by adding a DNA coding for such peroxisome-targeting signal to a gene coding for an enzyme involved in polyester synthesis, it becomes possible to localize the enzyme involved in polyester synthesis in peroxisomes for efficient polyester synthesis.

In plants, targeting of the PHA synthase gene toward peroxisomes results is reported (WO 99/35278).

Known as peroxisome-targeting signals occurring at the carboxyl terminus are sequences comprising three amino acid residues, namely "(serine/alanine/cysteine)-(lysine/arginine/histidine)-leucine". The expression (serine/alanine/cysteine), for instance, as used herein means any one of serine, alanine and cysteine. For the targeting of an enzyme involved in polyester synthesis toward peroxisomes, the addition of the above three-amino-acid sequence to the carboxyl terminus of the enzyme is sufficient. Among the peroxisome-targeting carboxyl-terminal signals, the most commonly known one, namely "serine-lysine-leucine" (hereinafter referred to as SKL for short) (SEQ ID NO:1) or the sequence "alanine-lysine-isoleucine" (hereinafter referred to as AKI for short) (SEQ ID NO:2), which is known as the peroxisome-targeting carboxyl-terminal signal in *Candida tropicalis* (J. D. Aitchison et al., J. Biol. Chem., 266, 23197-23203 (1991)), is preferably added to the carboxyl terminus.

The nucleotide sequence corresponding to such amino acid sequence is not particularly restricted. In the case of SKL, the nucleotide sequence shown under SEQ ID NO:3 can be utilized and, in the case of AKI, that shown under SEQ ID NO:4 can be used.

Further, sequences occurring in the vicinity of the N terminus and comprising 9 amino acid residues, namely "(arginine/lysine)-(leucine/valine/isoleucine)-(5 amino acid residues)-(histidine/glutamine)-(leucine/alanine)", are also known as peroxisome-targeting signals. By inserting and adding these sequences into an enzyme involved in polyester synthesis, it is possible to cause localization of the enzyme in peroxisomes.

The novel gene resulting from addition of a DNA coding for such a peroxisome-targeting signal as mentioned above to a gene coding for an enzyme involved in polyester synthesis can be constructed by chemical synthesis or by the PCR method, for instance. In the following, a method of adding SKL to the carboxyl terminus of the PHA synthase gene shown under SEQ ID NO:5 or the R-specific enoyl-CoA hydratase gene shown under SEQ ID NO:6, each as a gene for an enzyme involved in polyester synthesis, by PCR is described as an example.

A novel gene (hereinafter referred to as ORF2S for short) (SEQ ID NO:7) resulting from addition of a DNA coding for a peroxisome-targeting signal to the PHA synthase gene can be constructed by carrying out PCR using, as primers for PCR, oligonucleotides shown under SEQ ID NO:11 and SEQ ID NO:12 and, as a template, the PHA synthase gene shown under SEQ ID NO:5. In the same manner, a novel gene (hereinafter referred to as ORF3S for short) (SEQ ID NO:9) resulting from addition of a DNA coding for a peroxisome-targeting signal to the R-specific enoyl-CoA hydratase gene can be constructed by carrying out PCR using, as primers for PCR, oligonucleotides shown under SEQ ID NO:14 and SEQ ID NO:15 and, as a template, the R-specific enoyl-CoA hydratase gene shown under SEQ ID NO:6. The PCR conditions to be used here may be arbitrary provided that the target gene fragments can be amplified.

In the same manner as mentioned above, a DNA coding for AKI can be added to the carboxyl terminus of the PHA synthase gene or R-specific enoyl-CoA hydratase gene. By carrying out PCR using primers shown under SEQ ID NO:11 and SEQ ID NO:13 and the PHA synthase gene as a template, it is possible to construct a novel gene (hereinafter referred to as ORF2A) (SEQ ID NO:8). In the same way, by carrying PCR using primers shown under SEQ ID NO:14 and SEQ ID NO:16 and the R-specific enoyl-CoA hydratase gene as a template, it is possible to construct a novel gene (hereinafter referred to as ORF3A) (SEQ ID NO:10).

The nucleotide sequences of the above-mentioned novel genes shown under SEQ ID NO:7 to SEQ ID NO:10 may have undergone deletion, substitution and/or addition of one or a plurality of nucleotides respectively provided that the corresponding enzymes have substantial polyester synthesizing activity. The DNAs comprising the above nucleotide sequences may respectively be the DNAs capable of hybridizing with DNA, which comprises the sequences illustrated above as SEQ ID, in a stringent condition, provided that they can provide substantial enzyme activities.

The gene resulting from addition of a DNA coding a peroxisome-targeting signal to the genes coding for the above enzyme involved in polyester synthesis is a gene capable of being expressed in yeast. The "yeast" so referred to herein is not particularly restricted. Thus, usable are kinds of yeast deposited with organism depositories (e.g. IFO, ATCC, etc.) and belonging to such genera as *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkera, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblas-* tosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis, and Zygozyma.

Among the yeast described above, in view of high proliferation potency when fat and oils are used as carbon sources, high safety of strains, and the fact that separation of cells from culture fluid is relatively easy, preferably is one belonging to the genus *Candida* or *Yarrowia*, more preferably *Candida maltosa* or *Yarrowia lipolytica*, still more preferably *Candida maltosa*.

From the gene resulting from addition of a DNA coding for a peroxisome-targeting signal to the genes coding for an enzyme involved in polyester synthesis, there is translated the enzyme involved in polyester synthesis.

(3) Gene Expression Cassette Construction

For the above gene resulting from addition of a DNA coding for a peroxisome-targeting signal to a gene coding for an enzyme involved in polyester synthesis to be expressed in yeast, it is necessary that such DNA sequences as a promoter, UAS, occur on the 5' upstream of the gene and such DNA sequences as poly (A) additional signal, terminator, etc. on the 3' downstream of the gene. When an appropriate site satisfying the above conditions occurs on a yeast chromosome, the gene in question may be directly inserted therein. Alternatively, the gene may be inserted into a plasmid having an appropriate promoter and terminator so that yeast may be transformed with the resulting plasmid. In the practice of the present invention, a gene expression cassette is preferably constructed by joining a promoter to the gene on the 5' upstream thereof and a terminator on the 3' downstream thereof so that the cassette may be used in transforming yeast.

Any promoter and terminator sequences may be used provided that they can function in yeast. While, among the promoters, there are ones causing constitutive expression and ones causing inducible expression, either type of promoter may be used. In the practice of the present invention, it is desirable that the promoter and terminator can function in *Candida maltosa*, hence the promoter and terminator be derived from *Candida maltosa*. More preferably, the *Candida maltosa* ALK1, ALK5 or POX2 gene-derived promoter and the ALK1 gene-derived terminator are utilized.

Thus, for example, the promoter ALK1p (SEQ ID NO:17) of the *Candida maltosa* ALK1 gene (GenBank D00481), the promoter ALK5p (SEQ ID NO:18) of the ALK5 gene, and the promoter POX2p (SEQ ID NO:19) of the POX2 gene (GenBank D21228), among others, can be used as the promoter. The terminator ALK1t (SEQ IDNO:20) of the *Candida maltosa* ALK1 gene and the like can be used as the terminator. The nucleotide sequences of the above promoters and terminators each may have undergone deletion, substitution and/or addition of one or more nucleotides provided that they can function in *Candida maltosa*. The DNA comprising the above nucleotide sequences may respectively be the DNA capable of hybridizing in a stringent condition with DNA containing the sequences illustrated above as SEQ ID, provided that they can function in *Candida maltosa*.

The promoter is ligated to the 5' upstream of the gene coding for an enzyme involved in polyester synthesis with an added DNA coding for a peroxisome-targeting signal, and the terminator is ligated to the 3' downstream of the gene coding for the enzyme involved in polyester synthesis with the added peroxisome-targeting signal-encoding DNA.

The vector to be used in constructing the gene expression cassette may be any of those capable of autonomous replication in *Escherichia coli*. It may further have a region capable of autonomous replication in yeast. The vector capable of autonomous replication in yeast is maintained in microbial cells. It is also possible to integrate the gene expression cassette into a chromosome. As an example, pUTU1 capable of autonomous replication in *Candida maltosa* can be used (M. Ohkuma, et al., J. Biol. Chem., vol. 273, 3948-3953 (1998)).

Appropriate restriction enzyme sites for joining the promoter and terminator to the structural gene can be formed by utilizing the PCR method. The primer sequences to be used in PCR are not particularly restricted but, for example, the sequences shown under SEQ ID NO:21 to SEQ ID NO:28 can be used. The PCR conditions are arbitrary provided that the desired gene fragments can be amplified.

Although the method of constructing the gene expression cassette according to the present invention is not particularly restricted, a construction method in which the above-mentioned two genes, namely ORF2S and ORF3S, are used as the genes resulting from addition of a DNA sequence coding for a peroxisome-targeting signal to a gene coding for an enzyme involved in polyester synthesis is described below as an example.

(a) The Case of Using ALK1p, ALK5p and ALK1t

As for the promoter region, ALK1p whose 5' terminus is PvuII and 3' terminus is NdeI can be prepared using the ALK1 gene as a template, together with primers shown under SEQ ID NO:21 and SEQ ID NO:22. As for the terminator region, ALK1t whose 5' end is HindIII and 3' end is EcoRV can be prepared using the ALK1 gene as a template, together with primers shown under SEQ ID NO:27 and SEQ ID NO:28. Usable as the vectors are the vector pUTA1 (FIG. 1) constructed by using pUTU1 and the *Candida maltosa* ADE1 gene (SEQ ID NO:29) (GenBank D00855) (S. Kawai, et al., Agric. Biol. Chem., vol. 55, 59-65 (1991)) while changing the marker gene from uracil to adenine, and pUCNT (WO 94/03613).

ALK1p is joined to pUCNT at the PvuII-NdeI site to construct pUCNT-ALK1p, and ALK1t is ligated to pUCNT at the HindIII-EcoRV site to construct pUCNT-ALK1t. Then, ALK1p is excised from pUCNT-ALK1p with PvuII and NdeI, and joined to pUCNT-ALK1t at the PvuII-NdeI site. Thus, pUAL1 (FIG. 2) can be constructed.

Then, ORF2S is joined to pUAL1 at the NdeI-PstI site. Thus, a plasmid, pUAL-ORF2S (FIG. 3), can be constructed.

Further, ORF2S is excised, together with the upstream promoter and downstream terminator, from the plasmid pUAL-ORF2S using EcoT22I, followed by joining to pUTA1 at the PstI site, whereby pHA2S (FIG. 4) can be constructed.

The above construction scheme is summarized in FIG. 8 and FIG. 9. The symbol "*1" in FIG. 8 or 9 represents that this is where FIG. 8 or 9 are connected.

On the other hand, ALK5p (SEQ ID NO:18) whose 5' end is PvuII and 3' end is NdeI can be prepared using the *Candida maltosa* ALK5 gene (GenBank D12717) as a template, together with primers shown under SEQ ID NO:23 and SEQ ID NO:24. This DNA fragment is substituted for ALK1p in pUAL1, whereby pUAL5 can be constructed. The ALK5 promoter and ALK1 terminator are excised from this plasmid using PvuI and PvuII and joined to the commercial vector pSTV28 at the SmaI-PvuI site, whereby pSTAL5 can be constructed. ORF3S is joined to this plasmid at the NdeI-PstI site. Thus, pSTAL5-ORF3S (FIG. 5) can be constructed.

Further, ORF3S is excised, together with the upstream promoter and downstream terminator, from pSTAL5-ORF3S using SalI, followed by ligating to pHA2S at the SalI site, whereby a plasmid, pHA23S2 (FIG. 6), can be constructed.

The above construction scheme is summarized in FIG. 10 and FIG. 11. The symbol "*2" in FIG. 10 or 11 represents that this is where FIG. 10 or 11 are connected.

(b) The Case of Using ALK1p, POX2p and ALK1t

POX2p (SEQ ID NO:19) whose 5' end is PvuII and 3' end is NdeI can be prepared using the *Candida maltosa* POX2 gene (GenBank D21228) as a template, together with primers shown under SEQ ID NO:25 and SEQ ID NO:26. This DNA fragment is substituted for the lac promoter in pUCNT-ORF3St, whereby pPOX2-ORF3S can be constructed. ORF3S is excised, together with the upstream promoter and downstream terminator, from pPOX2-ORF3S using SalI, whereby plasmid pHA23S1 (FIG. 7), which is joined to pHA2S at the SalI site, can be constructed. The above construction scheme is summarized in FIG. 12.

In the above manner, the gene expression cassette for the production of a polyester resulting from homopolymerization or copolymerization of a 3-hydroxyalkanoic acid(s) represented by the general formula (1) in the yeast *Candida maltosa* can be constructed.

(4) Host

The "yeast" so referred to herein is not particularly restricted. Thus, usable are yeasts deposited with organism depositories (e.g. IFO, ATCC, etc.) and belonging to such genera as *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkera, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma.*

The yeast to be used as the transformant host in the practice of the present invention is not particularly restricted but, in view of high proliferation potency when fat and oils are used as carbon sources, high safety of strains, and the fact that separation of cells from culture fluid is relatively easy, preferably is one belonging to the genus *Candida* or *Yarrowia*, more preferably *Candida maltosa* or *Yarrowia lipolytica*, still more preferably *Candida maltosa*. Among the yeasts usable as hosts, the *Candida maltosa* AC16 strain has been internationally deposited with the National Institute of Advanced Industrial Science and Technology International Patent Organism Depositary, AIST Tsukuba Central 6, 1-1-1 Higashi, Tsukuba, Ibaraki, Japan, as of Nov. 15, 2000 under the accession number FERM BP-7366.

(5) Transformant Preparation

The transformant according to the present invention is yeast with one or more kind of genes, each resulting from addition of a DNA coding for a peroxisome-targeting signal to the gene coding for the above-mentioned enzyme involved in polyester synthesis, as introduced therein. It is preferred that one or more kind of enzyme gene expression cassettes for the production of enzyme(s) involved in polyester synthesis, which cassettes each comprises the above gene, a promoter and a terminator both capable of functioning in the yeast, are introduced in the yeast.

The gene expression cassette recombinant vector involved in polymer synthesis can be introduced into yeast in the conventional manner, using, for example, the calcium phosphate method (Lederberg, E. M. et al., J. Bacteriol., 119, 1072 (1974)) or the electroporation method (Current Protocols in Molecular Biology, vol. 1, 1.8, p. 4 (1994)). Commercially available transformation kits such as Fast Track TM-Yeast Transformation Kit SM (Geno Technology) can also be utilized.

As an example, the *Candida maltosa* CHA1 strain (S. Kawai, et al., Agric. Biol. Chem., vol. 55, 59-65 (1991)) can be used as the host. By transforming this strain using the gene expression cassette involved in polymer synthesis by the transformation method mentioned above, it is possible to produce *Candida maltosa* transformants having the above-mentioned plasmid pHA2S or pHA23S2, for instance.

Among such transformants, the *Candida maltosa* AC16 (pHA23S1) strain obtainable by transformation of the plasmid pHA23S1 has been internationally deposited with the National Institute of Advanced Industrial Science and Technology International Patent Organism Depositary, AIST Tsukuba Central No. 6, 1-1-1 Higashi, Tsukuba, Ibaraki, Japan, as of Oct. 3, 2001 under the accession number FERM BP-7762, and the *Candida maltosa* AC16(pHA23S2) obtainable by introduction of the plasmid pHA23S2 as of the same date under the accession number FERM BP-7763.

(6) Polyester Production

In accordance with the polyester production method of the present invention, a polyester is recovered from the culture obtainable by cultivating the above-mentioned transformant of the present invention.

Thus, the polyester production according to the present invention can be carried out by adding the above transformant to a culture medium, and cultivating the same, followed by recovering the product polyester from the cultured cells or culture obtained. The cultivation temperature is within a temperature range in which the organism can grow, preferably 15° C. to 40° C., more preferably 20° C. to 40° C., still more preferably 28° C. to 34° C. The cultivation time is not particularly restricted but, for example in the case of batch cultivation, preferably is about 1 to 7 days, and continuous cultivation also can be carried out.

The culture medium is not particularly restricted provided that the yeast can utilize the medium. Thus, for example, media containing a carbon source(s), a nitrogen source (s), inorganic salts, and other organic nutrient sources can be used.

The carbon source is not particularly restricted provided that the yeast can assimilate it. Thus, for example, carbohydrates, fats and oils, fatty acids, n-paraffins and the like can be used. As the carbohydrates, there may be mentioned, for example, glucose, sucrose, glycerol, etc. As the fats and oils, there may be mentioned, for example, rapeseed oil, coconut oil, palm oil, palm kernel oil, etc. As the fatty acids, there may be mentioned, for example, hexanoic acid, octanoic acid, decanoic acid, lauric acid, oleic acid, palmitic acid, linolic acid, linolenic acid, myristic acid, and like saturated and unsaturated acids, as well as esters and salts of these fatty acids and other fatty acid derivatives. As the n-paraffins, there may be mentioned, for example, dodecane, tetradecane, etc.

When the promoter expression is of the inducible type, an appropriate inducer (e.g. alcohol) is to be added. In some instances, the inducer may serve as the main carbon source.

As an example, *Candida maltosa* can be cultivated using fats or oils as carbon sources. In the case of yeast, which cannot assimilate fats or oils efficiently or at all, improvements can be achieved by adding lipase to the medium. Furthermore, yeast can be provided with the ability to assimilate fats and oils by transformation with a lipase gene.

Further, the proportion of a component(s) having a odd number of carbon atoms in the polyester carbon chain resulting from homopolymerization or copolymerization of 3-hydroxyalkalnoic acids represented by the general formula (1) can be increased by using, as carbon sources, fatty acids or n-paraffins whose carbon chain has an odd number of carbon atoms.

As the nitrogen source, there may be mentioned, for example, ammonia, ammonium chloride, di-ammonium sulfate, di-ammonium hydrogenphosphate, and other ammonium salts, as well as peptone, meat extract, yeast extract, and the like.

As the inorganic salts, there may be mentioned, among others, potassium dihydrogenphosphate, di-potassium hydrogenphosphate, magnesium hydrogenphosphate, magnesium sulfate, and sodium chloride.

The other organic nutrient sources include, among others, amino acids such as glycine, alanine, serine, threonine and proline; and vitamins such as vitamin B1, vitamin B12, biotin, nicotinamide, pantothenic acid, and vitamin C.

In the practice of the present invention, the polyester is recovered from yeast cells using the following method, for instance. After completion of cultivation, cells are separated from the culture fluid using a centrifuge, for instance, and the cells are washed with distilled water and methanol or the like, and then dried. The polyester is extracted from these dried cells using an organic solvent such as chloroform. The cell fraction is removed from the organic solvent solution containing the polyester by filtration, for instance. A poor solvent, such as methanol or hexane, is added to the filtrate to cause the polyester to precipitate out. The precipitate polyester is separated from the supernatant by filtration or centrifugation, and dried. The polyester can be thus recovered.

Since yeast cells are used as polyester producer cells in accordance with the present invention, such simple and easy methods of separation and recovery as mentioned above can be utilized.

The polyester obtained is analyzed by gas chromatography and/or nuclear magnetic resonance spectrometry, for instance.

The polyester production method according to the present invention has the constitution mentioned above and, therefore, can produce polyesters, which are homopolymers or copolymers of a 3-hydroxyalklanoic acid(s) represented by the general formula (1), with good productivity.

Further, by producing, using the above-mentioned plasmid pHA2S or the like, a transformant of *Candida maltosa* which has a gene resulting from addition of a DNA coding for a peroxisome-targeting signal to a gene coding for an enzyme involved in polyester synthesis, together with a promoter and terminator both capable of functioning in yeast, and cultivating the same, the copolyester P(3HB-co-3HH), which results from copolymerization of 3-hydroxybutyric acid represented by the formula (2) given herein above and 3-hydroxyhexanoic acid represented by the formula (3) given above, can be produced.

BEST MODE FOR CARRYING OUT THE INVENTION

Figure 1:
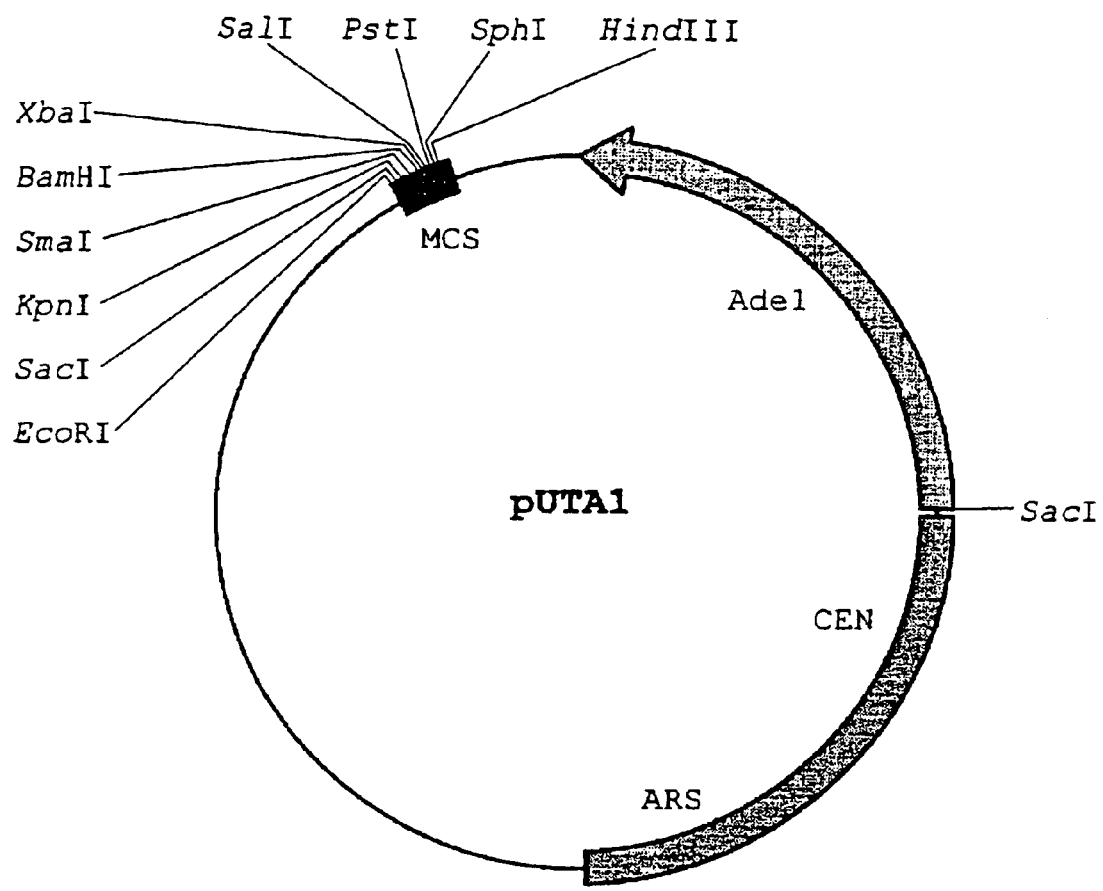
FIG. 1 is a schematic diagram of the plasmid pUTA1 used as a vector as described in the example section.

The following examples illustrate the present invention more specifically. These examples are, however, by no means limitative of the technical scope of the present invention.

EXAMPLE 1

Designing and Synthesis of Genes Involved in Polyester Synthesis

Based on the amino acid sequences of *Aeromonas caviae*-derived PHA synthase and R-specific enoyl-CoA hydratase (T. Fukui, et al., FEMS Microbiology Letters, vol. 170, 69-75 (1999)), which converts the β oxidation cycle intermediate enoyl-CoA to the monomer (R)-3-hydroxyacyl-CoA, the corresponding enzyme genes involved in polyester synthesis were synthesized.

Since *Candida maltosa* is yeast translating the CTG codon into serine, not leucine, CTG was not assigned to the leucine codon. That codon with high codon usage in *Candida maltosa* was preferentially selected as the codon corresponding to each amino acid. For codon usage, Klaus Wolf: Nonconventional Yeasts in Biotechnology (published by Springer) was referred to.

The gene designing was carried out in the following manner. Based on the DNA sequences and amino acid sequences of *Aeromonas caviae*-derived PHA synthase and R-specific enoyl-CoA hydratase, which converts the β oxidation cycle intermediate enoyl-CoA to the monomer (R)-3-hydroxyacyl-CoA, optimal codons were assigned to the respective amino acids.

Further, for creating two KpnI sites in the DNA sequence for *Aeromonas caviae*-derived PHA synthase, the 969th T was modified into C, and the 1449th T into C.

The above substitutions in the above gene do not change the corresponding amino acid sequence.

In this way, the PHA synthase gene (ORF2) (SEQ ID NO:5) and R-specific enoyl-CoA hydratase gene (ORF3) (SEQ ID NO:6) were designed and chemically synthesized.

EXAMPLE 2

Construction of An Enzyme Gene Expression Cassette Involved in Polyester Synthesis (a) The case of using ALK1p, ALK5p and ALK1t For causing expression of ORF2 and ORF3 in *Candida maltosa*, it was decided that a *Candida maltosa*-derived promoter be ligated to the 5' upstream of each gene, and a *Candida maltosa*-derived terminator to the 3' downstream of each gene. Thus, the ALK1 gene (GenBank D00481) promoter ALK1p (SEQ ID NO:17) was selected for joining to ORF2, and the ALK5 gene (GenBank D12717) promoter ALK5p (SEQ ID NO:18) for joining to ORF3. The *Candida maltosa* ALK1 gene terminator ALK1t (SEQ ID NO:20) was selected for joining to the 3' downstream of each. For producing restriction enzyme recognition sites for joining the promoter and terminator to the structural gene, the PCR method was utilized. The primer sequences used for PCR are shown under SEQ ID NO:21 to SEQ ID NO:28. As for the PCR conditions, 25 cycles each comprising 1 minute at 94° C., 2 minutes at 55° C. and 3 minutes at 72° C. were repeated to amplify each gene fragment. The polymerase used was Takara Shuzo's ExTaq.

As for ALK1p, ALK1p whose 5' terminus is PvuII and 3' terminus is NdeI was prepared using the ALK1 gene as a template and using SEQ ID NO:21 and SEQ ID NO:22. As for ALK5p, ALK5p whose 5' terminus is PvuII and 3' terminus is NdeI was prepared using the ALK5 gene as a template and using SEQ ID NO:23 and SEQ ID NO:22. As for ALK1t, ALK1t whose 5'terminus is HindIII and 3' terminus is EcoRV was prepared using the ALK1 gene as a template and using SEQ ID NO:27 and SEQ ID NO:28.

Used as the vector for finally ligating with ORF2 or ORF3 was the vector pUTA1 (FIG. 1), wherein the marker gene is changed from uracil to adenine, constructed by using pUTU1 (M. Ohkuma, et al., J. Biol. Chem., vol. 273, 3948-3953 (1998)) produced by joining the *Candida maltosa*-derived autonomously replicating sequence (ARS) (GenBank D29758) and the URA3 gene (GenBank D12720) to pUC19 (Takara Shuzo), and the *Candida maltosa* ADE1 gene (SEQ ID NO:29) (GenBank D00855) (S. Kawai, et al., Agric. Biol. Chem., vol. 55, 59-65 (1991)).

Figure 2:
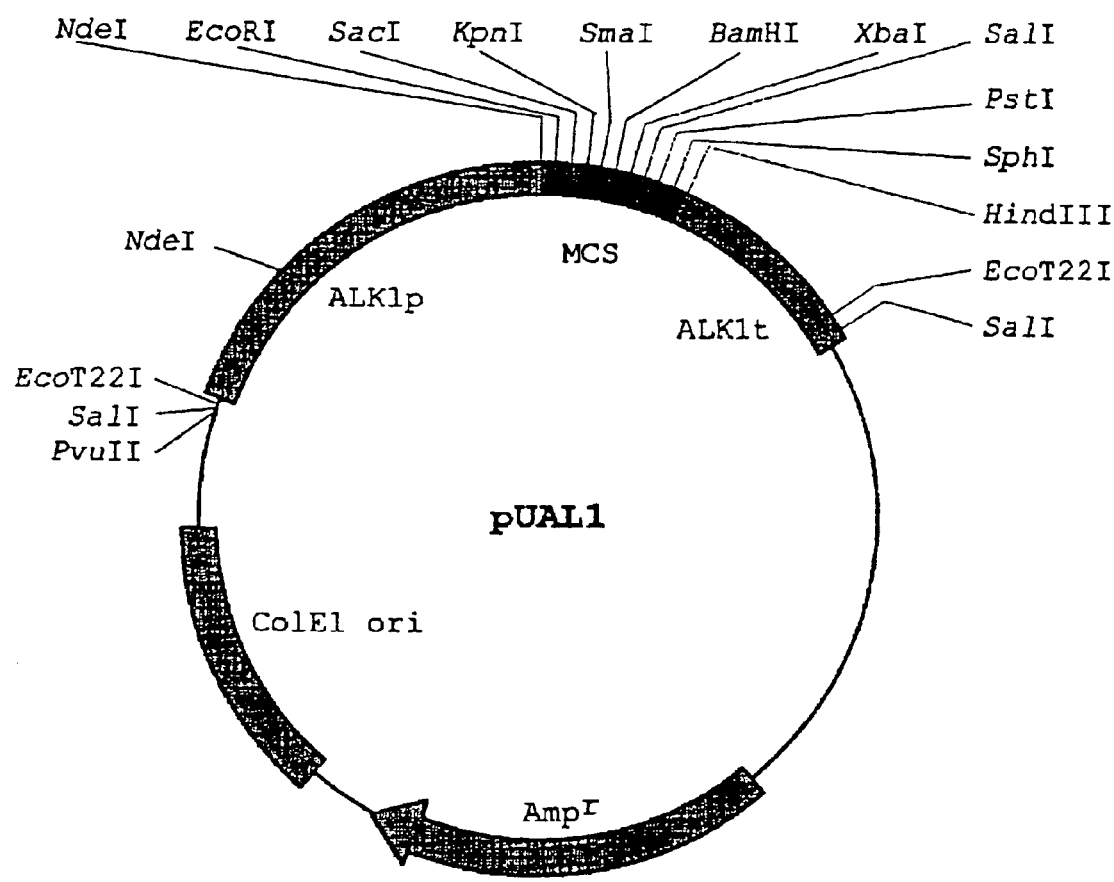
FIG. 2 is a schematic diagram of the plasmid pUAL1 constructed as described in the example section.

Then, pUCNT-ALK1p was constructed by joining ALK1p to pUCNT (WO 94/03613) at the PvuII-NdeI site. pUCNT-ALK1t was also constructed by joining ALK1t to pUCNT at the HindIII-SspI site. ALk1p was excised from pUCNT-ALK1p with PvuII and NdeI and joined to pUCNT-ALK1t at the PvuII-NdeI site to thereby construct pUAL1 (FIG. 2).

It was decided that a peroxisome-targeting signal be added to the carboxy terminus of each of the above-mentioned ORF2 and ORF3 so that each of them may be expressed in *Candida maltosa* and targeted to peroxisomes. Used as the peroxisome-targeting signal to be added to the carboxy terminus was the amino acid sequence Ser-Lys-Leu (SKL) or Ala-Lys-Ile (AKI). Sequences of the genes (ORF2S, ORF2A, ORF3S, and ORF3A) obtained by adding these amino acids to the ORF2 or ORF3 gene are shown under SEQ ID NO:7 to SEQ ID NO:10. With the ORF2 DNA as a template, ORF2S was constructed using the primers shown under SEQ ID NO:11 and SEQ ID NO:12, and ORF2A was constructed using the primers shown under SEQ ID NO:11 and SEQ ID NO:13. Similarly, with the ORF3 DNA as a template, ORF3S was constructed using the primers shown under SEQ ID NO:14 and SEQ ID NO:15, and ORF3A using the primers shown under SEQ ID NO:14 and SEQ ID NO:16. The PCR conditions were the same as mentioned above.

Figure 3:
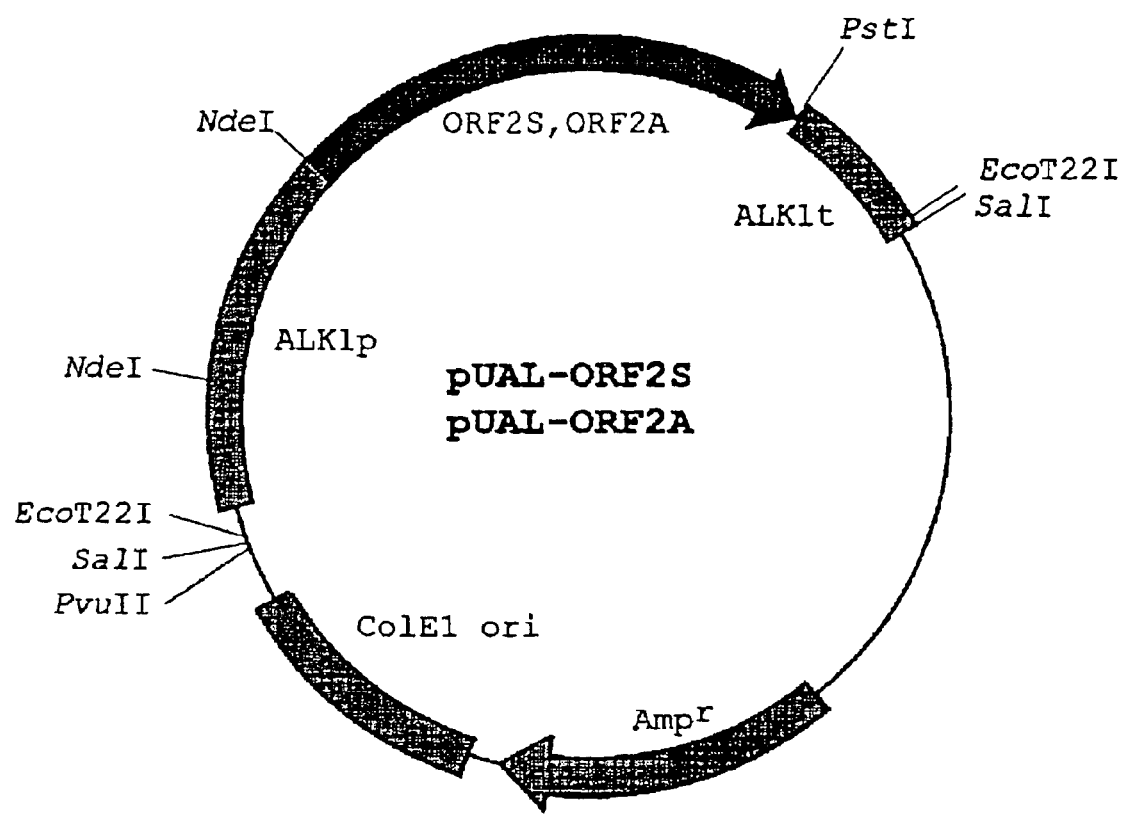
FIG. 3 is a schematic diagram of the plasmids pUAL-ORF2S and pUAL-ORF2A constructed as described in the example section.

The DNAs amplified were treated with NdeI and PstI, and ORF2S was joined to pUAL1 at the NdeI-PstI site to construct the plasmid pUAL-ORF2S, and pUAL-ORF2A (FIG. 3) was constructed in the same manner. ORF3S was joined to pUCNT-ALK1t at the NdeI-PstI site to construct pUCNT-ORF3St. ORF3A was constructed in the same manner as ORF3S.

Figure 4:
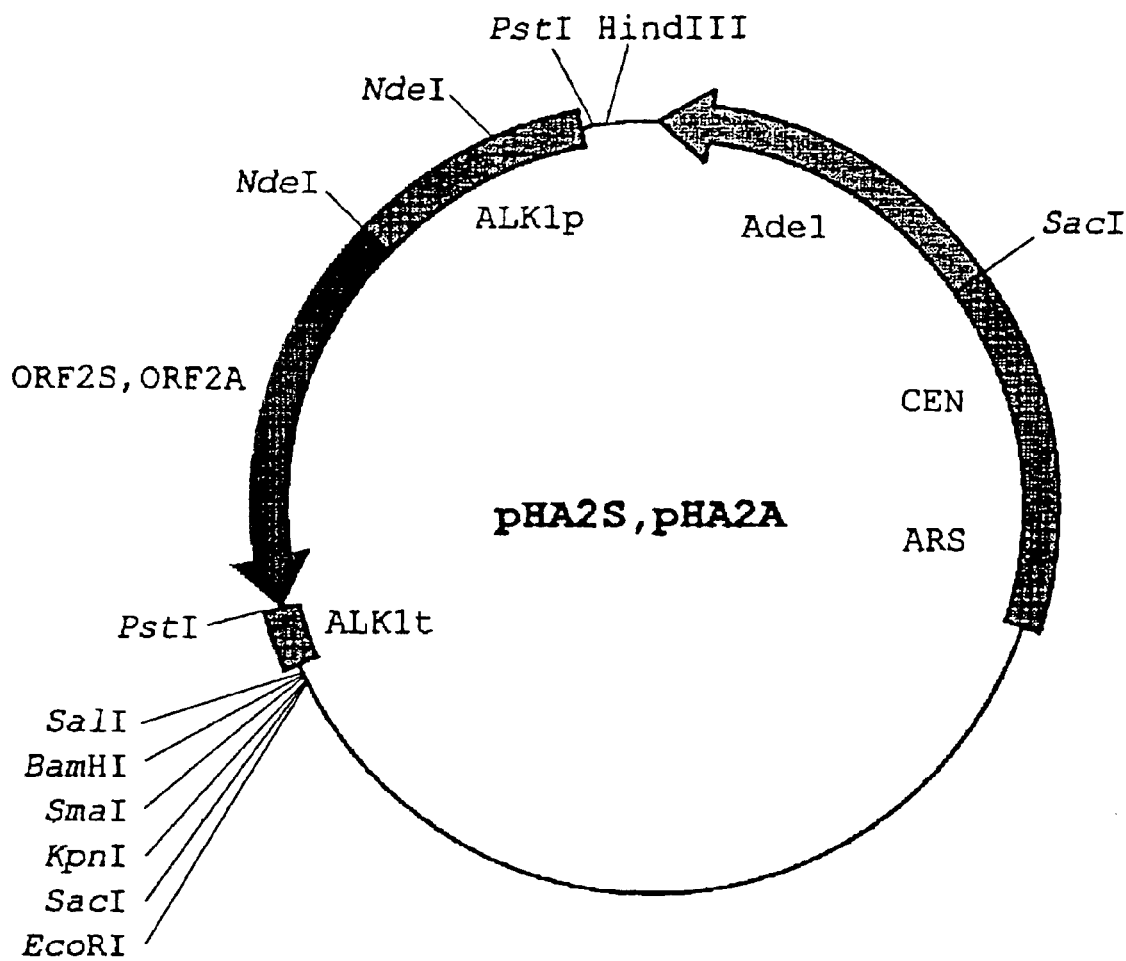
FIG. 4 is a schematic diagram of the plasmids pHA2S and pHA2A constructed as described in the example section.

ORF2S or ORF2A was excised, together with the upstream promoter and downstream terminator, from the plasmid pUAL-ORF2S or pUAL-ORF2A using EcoT22I, and joined to pUTA1 at the PstI site. pHA2S and pHA2A were thus constructed (FIG. 4).

Figure 5:
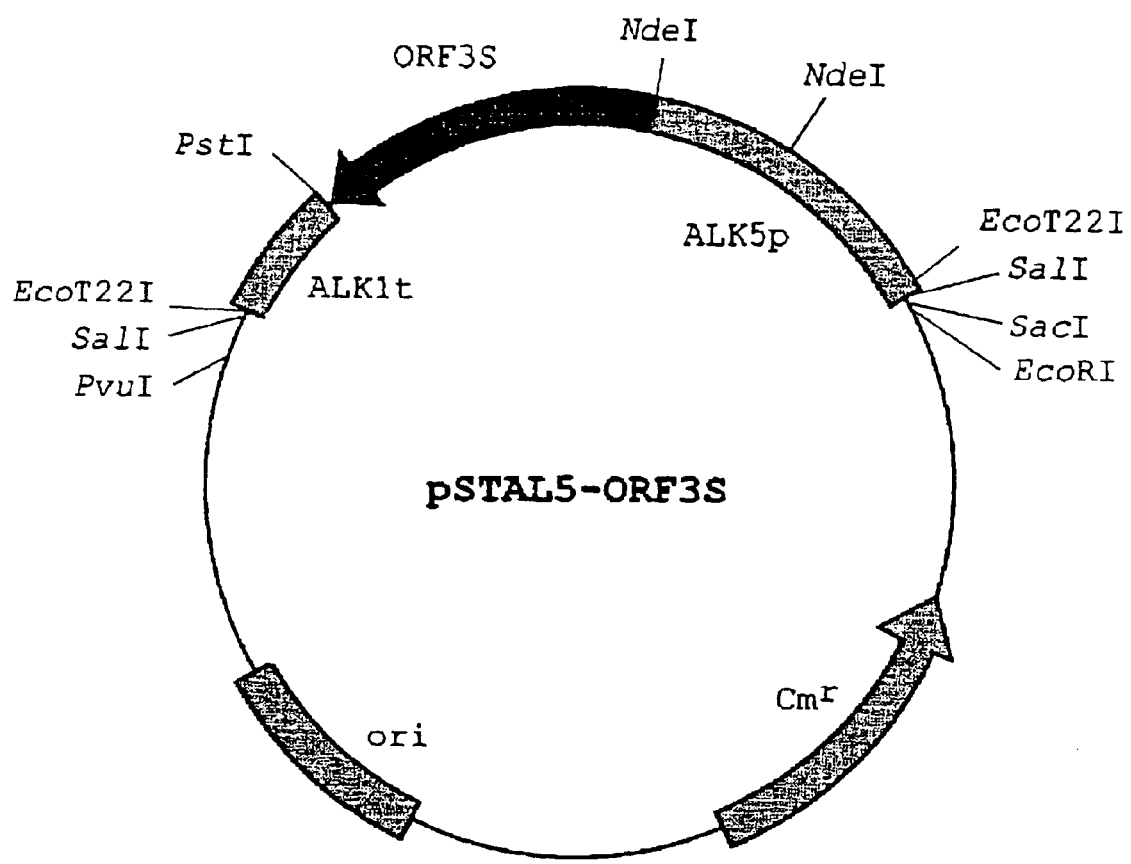
FIG. 5 is a schematic diagram of the plasmid pSTAL5-ORF3S constructed as described in the example section.

ALK5p (SEQ ID NO:18) whose 5' terminus is PvuII and 3' terminus is NdeI was constructed using SEQ ID NO;23 and SEQ ID NO:24 with the *Candida maltosa* ALK5 gene (GenBank D12717) as a template. This DNA fragment was substituted for ALK1p in pUAL1, whereby pUAL5 was constructed. The ALK5 promoter and ALK1 terminator were excised from this plasmid using PvuI and PvuII and joined to pSTV28 (product of Takara Shuzo) at the SmaI-PvuI site to construct pSTAL5. ORF3S was joined to this plasmid at the NdeI-PstI site, whereby pSTAL5-ORF3S (FIG. 5) was constructed.

Figure 6:
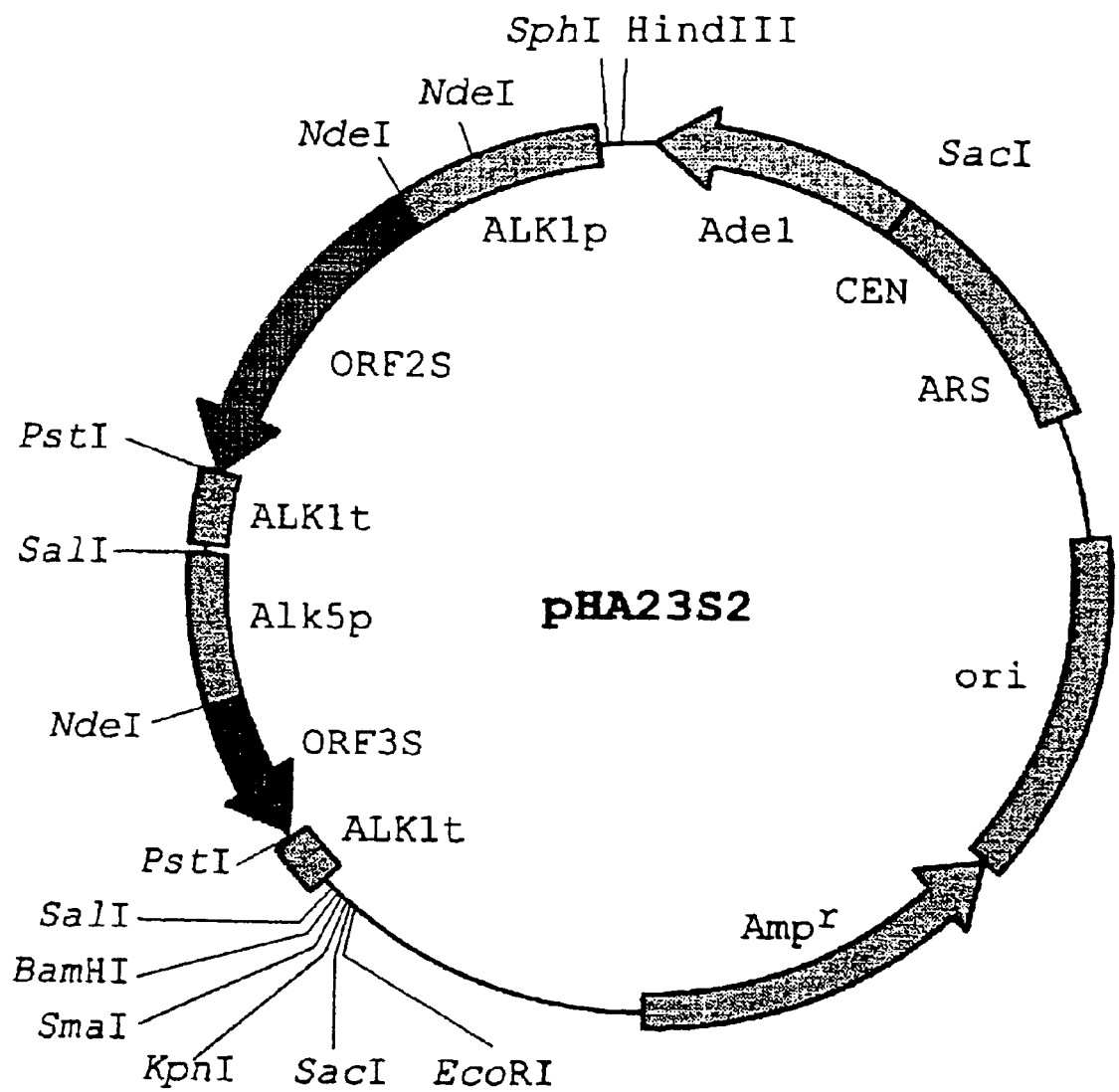
FIG. 6 is a schematic diagram of the plasmid pHA23S2 constructed as described in the example section.

ORF3S was excised, together with the upstream promoter and downstream terminator, from pSTAL5-ORF3S using SalI and joined to pHA2S at the SalI site to construct the plasmid pHA23S2 (FIG. 6).

(b) The Case of Using ALK1p, POX2p and ALK1t

Figure 7:
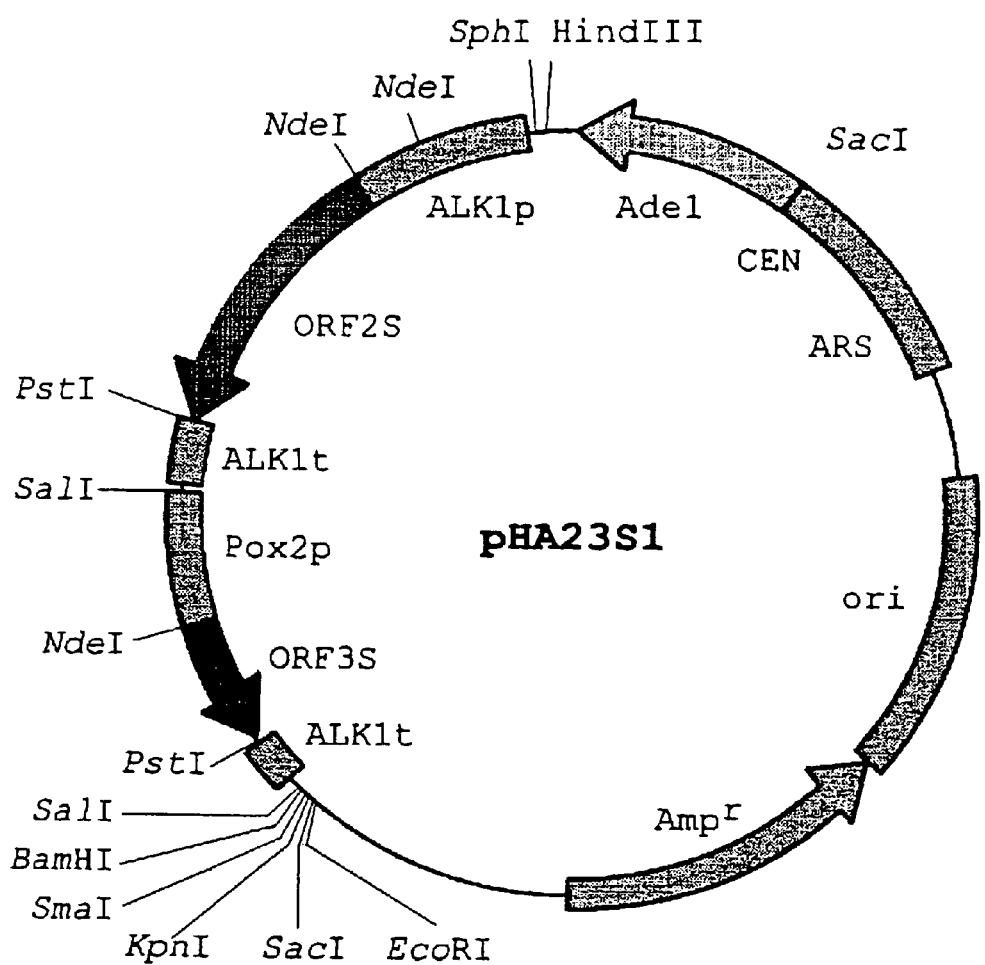
FIG. 7 is a schematic diagram of the plasmid pHA23S1 constructed as described in the example section.
Figure 8:
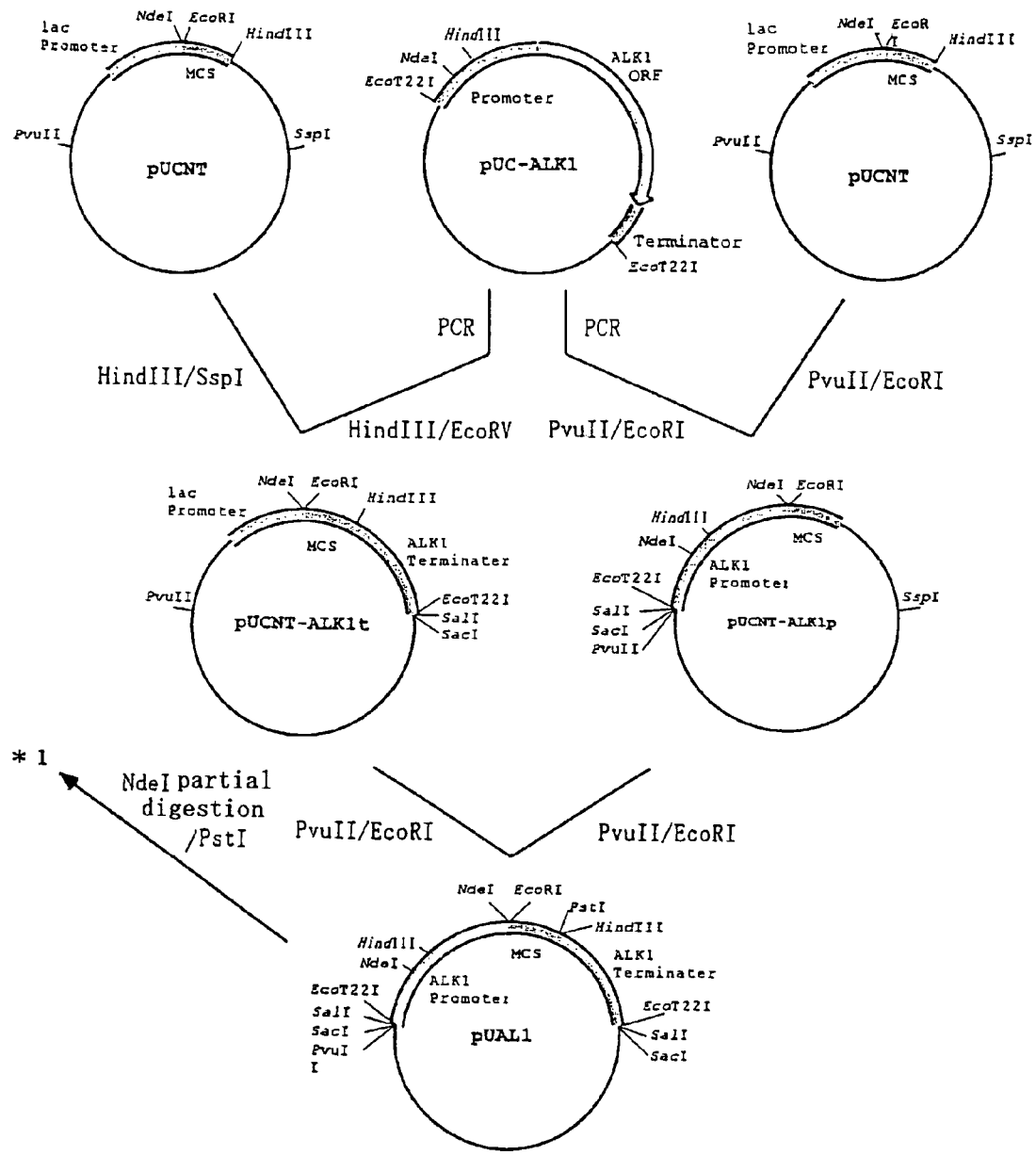
FIG. 8 and FIG. 9 show a plasmid construction scheme illustrating the methods of construction of the plasmids pHA2S and pHA2A for use in producing transformants of the present invention.
Figure 9:
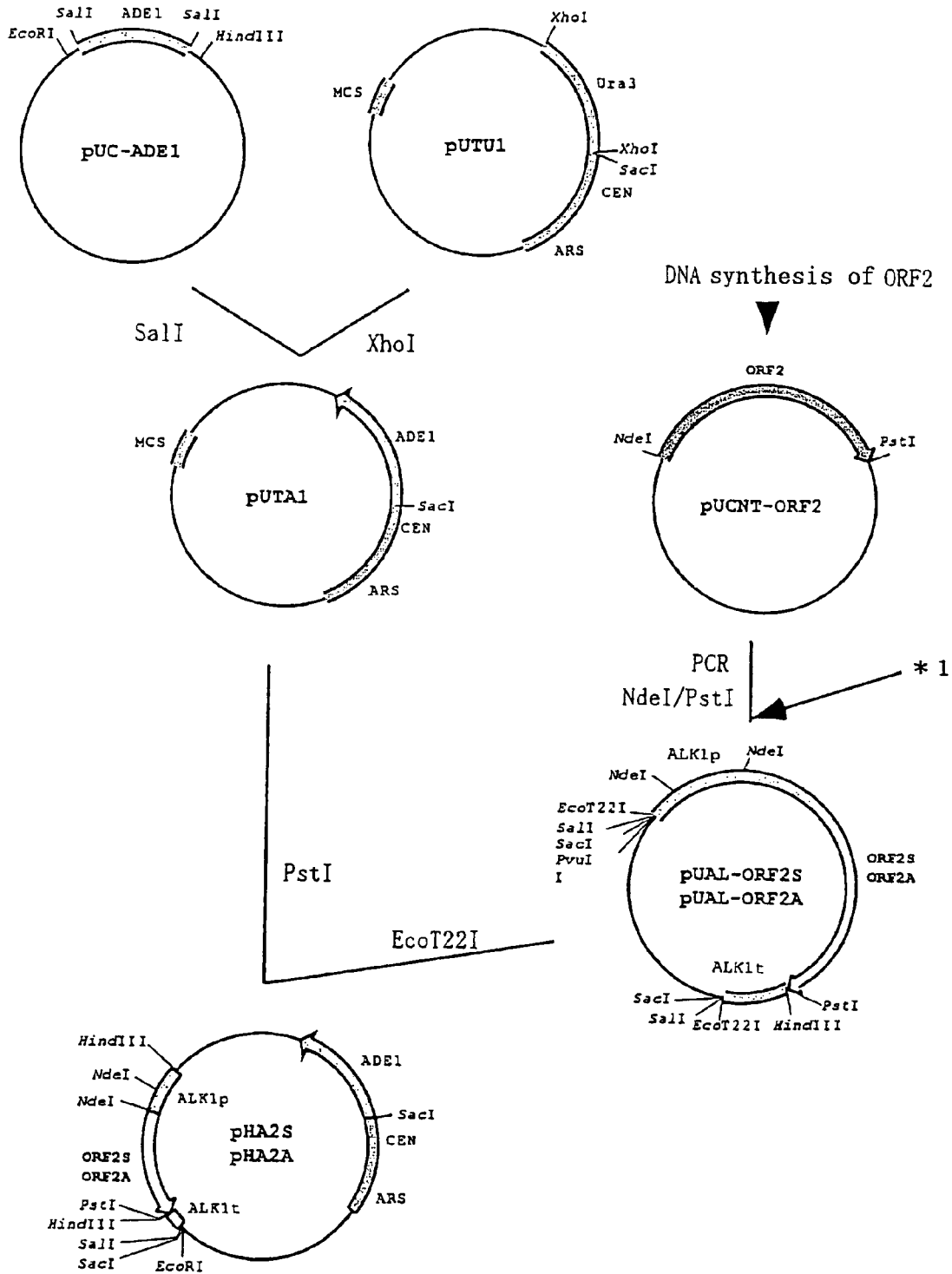
Figure 10:
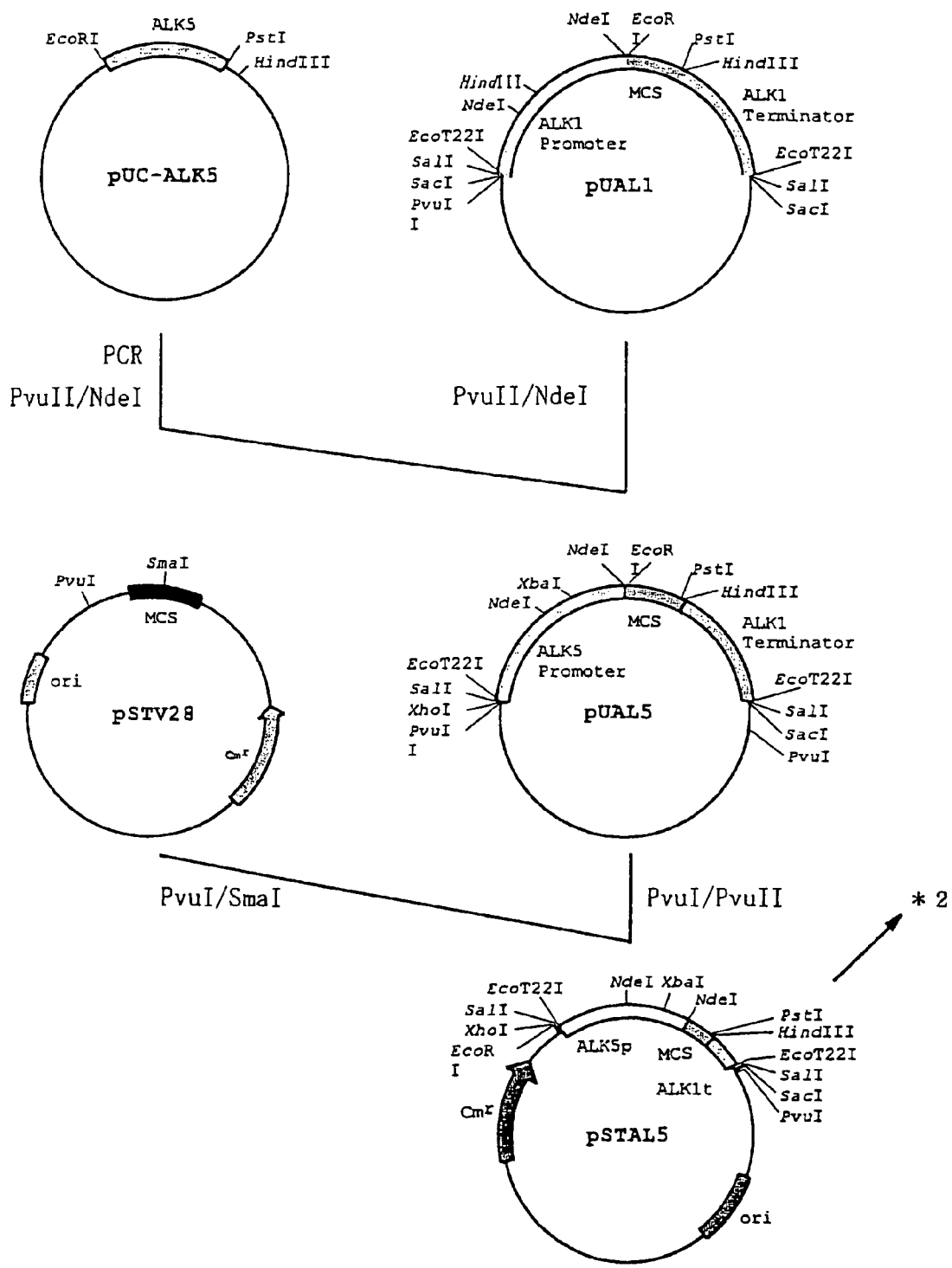
FIG. 10 and FIG. 11 show a plasmid construction scheme illustrating the method of construction of the plasmid pHA23S2 for use in producing transformants of the present invention.
Figure 11:
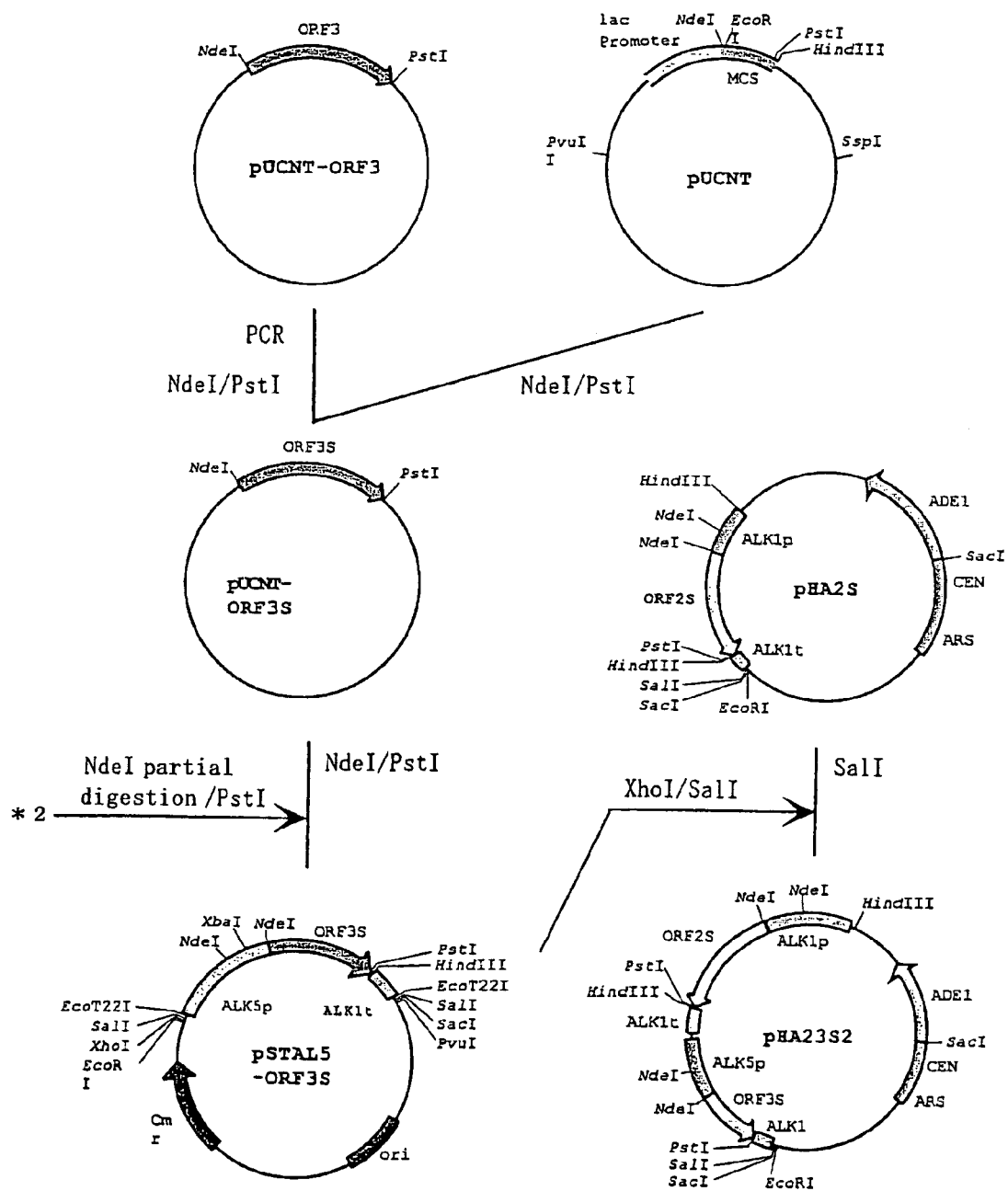
Figure 12:
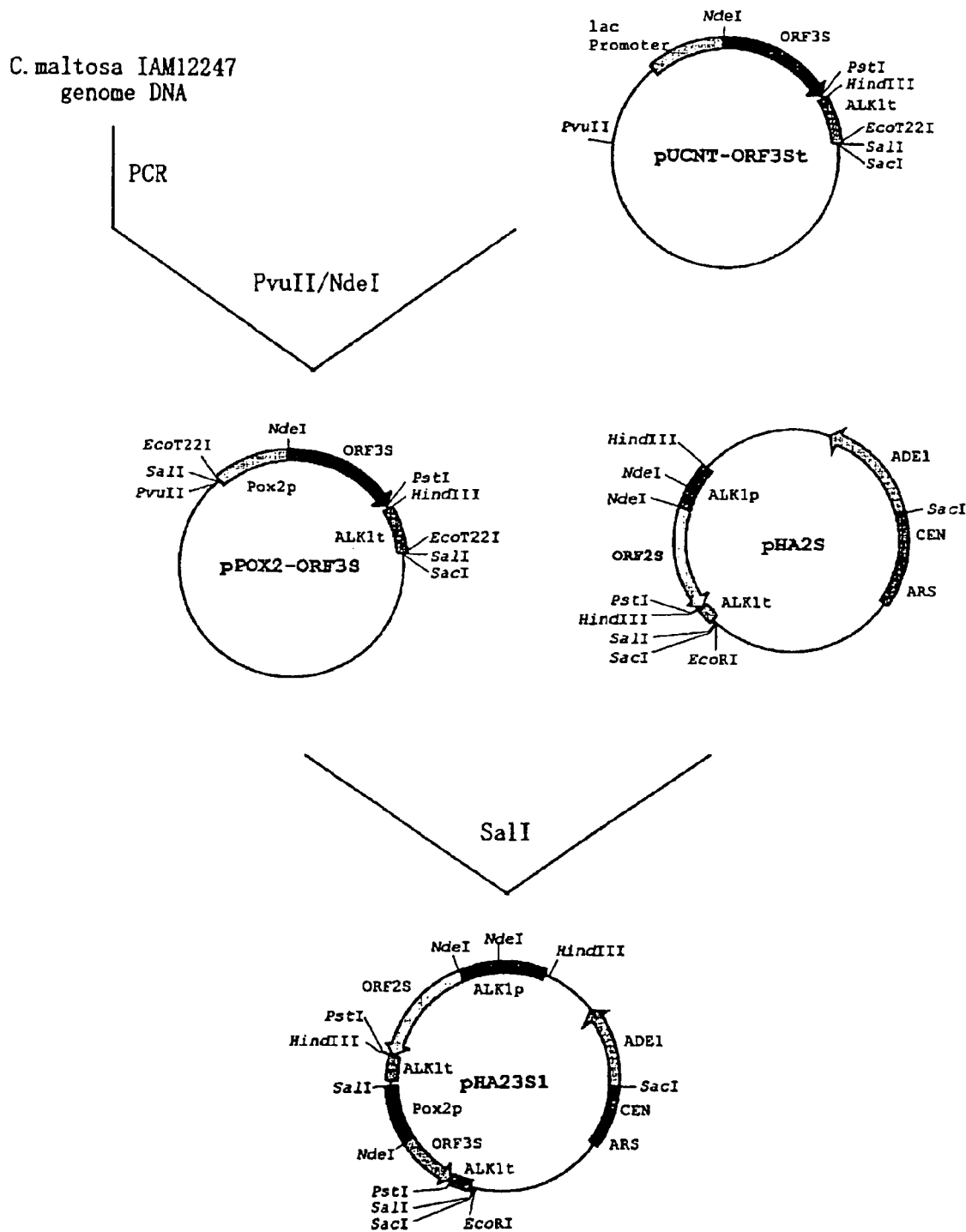
FIG. 12 shows a plasmid construction scheme illustrating the method of construction of the plasmid pHA23S1 for use in producing transformants of the present invention.

Based on the *Candida maltosa* POX2 gene (GenBank S21228), the primers shown under SEQ ID NO:25 and SEQ ID NO:26 were designed. Using these, with the *Candida maltosa* IAM 12247 genomic DNA as a template, POX2p (SEQ ID NO:19) whose 5' terminus is PvuII and 3' terminus is NdeI was prepared. This DNA fragment was substituted for the lac promoter in pUCNT-ORF3St to construct pPOX2-ORF3S. ORF3S was excised, together with the upstream promoter and downstream terminator, from pPOX2-ORF3S using SalI and joined to pHA2S at the SalI site, whereby the plasmid pHA23S1 (FIG. 7) could be constructed.

The preparation schemes for all the above plasmids are shown in FIG. 8 to FIG. 12.

EXAMPLE 3

Transformant Construction

Unless otherwise specified, the reagents used in yeast cultivation were commercial products available from Wako Pure Chemical Industries. In the practice of the present invention, a number of commercial kits were used. Unless otherwise specified, they were used according to the manuals attached thereto.

The host used was the *Candida maltosa* AC16 strain, which is a strain with the ADE1 gene disrupted and has been internationally deposited with the National Institute of Advanced Industrial Science and Technology International Patent Organism Depositary (accession number FERM BP-7366), and the above-mentioned gene expression cassettes of the present invention, namely the plasmids pHA2S, pHA2A, pHA23S1, and pHA23S2, were respectively introduced into the host. Each plasmid constructed was introduced into the host by the electroporation technique. The gene transfer apparatus used was ELECTRO CELL MANIPULATOR 600 (product of BTX). The cuvettes used were BM 6200 cuvettes produced by BIO MEDICAL CORPORATION CO. LTD. Each plasmid (1 μl) was added to 100 μl of competent cells. 100 μl of the thus-prepared competent cell/plasmid solution was taken and poured into a cuvette, which was set on the pulse generator. Then, electric pulses were applied under the following conditions: electrostatic capacity 40 μF, resistance value 246 ohm, and voltage 1.9 kV. After pulse application, 1 ml of 1 M sorbitol was added to each cuvette and, after gentle mixing, the cuvette was allowed to stand at room temperature for 1 hour. After plasmid introduction, the cells were cultured on a selective plate (0.67 w/v % Yeast Nitrogen base without amino acid (product of Difco), 2 w/v % glucose, 2 w/v % agar), to give transformants. Among the transformants obtained, the one harboring the plasmid pHA23S1 has been internationally deposited as *Candida maltosa* AC16(pHA23S1) with the National Institute of Advanced Industrial Science and Technology International Patent Organism Depositary under the accession number FERM BP-7762, and the one harboring the plasmid pHA23S2 as *Candida maltosa* AC16(pHA23S2) under the accession number FERM BP-7763.

EXAMPLE 4

Polymer Production Using the Transformants (a) Polymer Production Using the Transformants Resulting From Introduction of the Plasmid pHA2S or pHA2A The *Candida maltosa* transformants resulting from introduction of the gene necessary for polymer production were cultivated in the following manner. YNB medium (0.67 w/v % Yeast Nitrogen base without amino acid) supplemented with 1 w/v % of casamino acids and 1 v/v % of tetradecane was used as the medium.

A 500-ml Sakaguchi flask containing 50 ml of the above medium was inoculated with 500 μl of a glycerol stock of each transformant and, after 20 hours of cultivation, the culture was inoculated into a 2-L Sakaguchi flask containing 300 mL of the production medium at an inoculum size of 10 v/v %. This was cultivated at an incubation temperature of 30° C. and a shaking speed of 90 rpm for 4 days. Cells were recovered from the culture fluid by centrifugation, suspended in 80 ml of distilled water, and disrupted using an ultrahigh pressure homogenizer (APV's Rannie 2000, at 15,000 Psi for 15 minutes), followed by centrifugation. The precipitate obtained was washed with methanol and then lyophilized.

The lyophilized cells were ground, 100 ml of chloroform was added thereto, and the mixture was stirred overnight for effecting extraction. The cells were removed by filtration, the filtrate was concentrated to 1 to 2 ml using an evaporator, and about 10 ml of hexane was added to the concentrate to cause the polymer P(3HB-co-3HH) to precipitate out. The cultivation results thus obtained are shown in Table 1.

TABLE 1

Cultivation results with pHA2S and pHA2A

| Plasmid | Cell amount (g/L) | Polymer content (wt %) | 3HH composition (mol %) |
|---|---|---|---|
| pHA2S | 6.97 | 3.2 | 12 |
| pHA2A | 7.53 | 0.49 | 8.6 |

(b) Polymer Production Using the Transformants Resulting From Introduction of the Plasmid pHA2S, pHA23S1 or pHA23S2

YNB medium (0.67 w/v % Yeast Nitrogen base without amino acid) supplemented with 2 v/v % of dodecane or 2 v/v % of coconut oil was used as the medium.

The cultivation conditions were the same as described above under (a) except that the cultivation period was 2 days. The polymer P(3HB-co-3HH) was extracted in the same manner as described above under (a). The cultivation results are shown in Table 2.

TABLE 2

Cultivation results with pHA2S, pHA23S1 and pHA23S2

| Plasmid | Carbon source | Cell amount (g/L) | Polymer content (wt %) |
|---|---|---|---|
| pHA2S | Dodecane | 4.89 | 5.36 |
| | Coconut oil | 5.14 | 0.95 |
| pHA23S1 | Dodecane | 4.48 | 9.38 |
| | Coconut oil | 5.89 | 1.47 |
| pHA23S2 | Dodecane | 5.85 | 6.15 |
| | Coconut oil | 5.58 | 1.50 |

COMPARATIVE EXAMPLE 1

Cultivation was carried out in the same manner as described in Example 4 (a) except using the transformant (cell amount: 10.3 g/L) in which a plasmid pUTA-ORF23(WO01/88144), constructed by a polyester synthase gene incapable of adding a DNA coding for a peroxisome-targeting signal, was transformed. As a result, the content of the polymer P(3HB-co-3HH) was 0.1% by weight.

As described above, by constructing polyester synthase gene involved in polyester synthesis by adding a DNA coding a peroxisome-targeting signal, transforming a enzyme gene expression cassette containing that gene, promoter and terminator into yeast, and cultivating the thus-obtained transformant, it becomes possible to produce greater amount of polyester compared with the case which a polyester synthase gene incapable of adding a DNA coding for a peroxisome-targeting signal is used.

INDUSTRIAL APPLICABILITY

The present invention makes it possible to produce polyesters resulting from homopolymerization or copolymerization of a 3-hydroxyalkanoic acid(s) represented by the general formula (1) and having biodegradability and good physical properties by using yeast with high productivity.

The invention claimed is:

1. An isolated gene capable of being expressed in yeast, which is obtainable by fusion of a DNA coding for a peroxisome-targeting signal to a gene coding for an enzyme involved in polyester synthesis, wherein the enzyme involved in polyester synthesis is a polyhydroxyalkanoic acid synthase and wherein the polyhydroxyalkanoic acid synthase is encoded by a gene comprising the nucleotide sequence shown under SEQ ID NO:5.

2. The isolated gene according to claim 1,
wherein the peroxisome-targeting signal comprises the amino acid sequence shown under SEQ ID NO:1 or SEQ ID NO:2.

3. The isolated gene according to claim 1,
wherein the peroxisome-targeting signal-encoding DNA has the nucleotide sequence shown under SEQ ID NO:3 or SEQ ID NO:4.

4. The isolated gene according to claim 1,
which comprises the nucleotide sequence shown under SEQ ID NO:7 or SEQ ID NO:8.

5. A transformant resulting from transformation of the gene according to claim 1 into yeast.

6. A transformant according to claim 5 further comprising a promoter and a terminator capable of functioning in the yeast.

7. The transformant according to claim 6,
wherein the promoter and terminator are derived from *Candida maltosa*.

8. The transformant according to claim 6,
wherein the promoter is derived from *Candida maltosa* ALK1, ALK5 or POX2.

9. The transformant according to claim 6,
wherein the terminator is derived from *Candida maltosa* ALK1.

10. The transformant according to claim 5,
which is derived from a yeast species selected from the group consisting of the genus *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkera, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Kipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma.*

11. The transformant according to claim 10,
wherein the yeast belongs to the genus *Candida* or *Yarrowia*.

12. The transformant according to claim 11,
wherein the yeast is *Candida maltosa*.

13. The transformant according to claim 5,
wherein the polyester is a homopolymer or copolymer of a 3-hydroxyalkanoic acid(s) represented by the general formula (1):

R—HCOH—CH$_2$—COOH—    (1)

wherein R represents an alkyl group.

14. The transformant according to claim 5,
wherein the polyester is a copolyester, P(3HB-co-3HH), obtainable by copolymerization of 3-hydroxybutyric acid represented by the formula (2):

CH$_3$—HCOH—CH$_2$—COOH    (2)

and 3-hydroxyhexanoic acid represented by the formula (3):

C$_3$H$_7$—HCOH—CH$_2$—COOH    (3).

15. The method of producing a polyester which is a homopolymer or copolymer of a 3-hydroxyalkanoic acid using the transformant according to claim 5,
which method comprises cultivating the transformant and recovering the product polyester from the culture obtained.

* * * * *

SEQUENCE LISTING

<160> NUMBER OF SEQ ID NOS: 29

<210> SEQ ID NO 1
<211> LENGTH: 3
<212> TYPE: PRT
<213> ORGANISM: Artificial Sequence
<220> FEATURE:
<223> OTHER INFORMATION: Synthetic Peroxisome Targetting Sequence

<400> SEQUENCE: 1

Ser Lys Leu

<210> SEQ ID NO 2
<211> LENGTH: 3
<212> TYPE: PRT
<213> ORGANISM: Artificial Sequence
<220> FEATURE:
<223> OTHER INFORMATION: Synthetic Peroxisome Targetting Sequence

<400> SEQUENCE: 2

Ala Lys Ile

<210> SEQ ID NO 3
<211> LENGTH: 9
<212> TYPE: DNA
<213> ORGANISM: Artificial Sequence
<220> FEATURE:
<223> OTHER INFORMATION: Synthetic DNA

<400> SEQUENCE: 3 tctaaattg                                                               9

<210> SEQ ID NO 4
<211> LENGTH: 9
<212> TYPE: DNA
<213> ORGANISM: Artificial Sequence
<220> FEATURE:
<223> OTHER INFORMATION: Synthetic DNA

<400> SEQUENCE: 4 gctaaaatt                                                               9

<210> SEQ ID NO 5
<211> LENGTH: 1785
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(1785)

<400> SEQUENCE: 5

```
atg tct caa cca tct tat ggt cca ttg ttc gaa gct ttg gct cat tac      48 aat gat aaa ttg ttg gct atg gct aaa gct caa acc gaa aga act gct      96 caa gcc ttg ttg caa act aac ttg gat gat ttg ggt caa gtt ttg gaa     144 caa ggt tct caa caa cca tgg caa ttg att caa gct caa atg aat tgg     192 tgg caa gat caa tta aaa ttg atg caa cac act ttg tta aaa tct gct     240 ggt caa cca tct gaa cca gtt att act cca gaa aga tct gat aga aga     288 ttt aaa gct gaa gct tgg tct gaa caa cca att tat gat tac tta aaa     336
```

| | |
|---|---|
| caa tcc tat ttg tta act gct aga cat ttg ttg gct tct gtt gat gct | 384 |
| ttg gaa ggt gtc cca caa aaa tct aga gaa aga ttg aga ttc ttt act | 432 |
| aga caa tac gtc aac gct atg gct cca tct aat ttc ttg gct act aac | 480 |
| cca gaa ttg tta aaa ttg act ttg gaa tcc gat ggt caa aat ttg gtt | 528 |
| aga ggt ttg gct tta ttg gct gaa gat ttg gaa aga tct gct gat caa | 576 |
| tta aac att aga ttg act gat gaa tcc gct ttt gaa tta ggt aga gat | 624 |
| ttg gct ttg act cca ggt aga gtt gtt caa aga act gaa tta tat gaa | 672 |
| tta att caa tac tct cca act act gaa acc gtt ggt aaa acc cca gtt | 720 |
| ttg atc gtt cca cca ttc att aat aaa tat tac att atg gat atg aga | 768 |
| cca caa aac tcc ttg gtc gct tgg ttg gtc gct caa ggt caa acc gtt | 816 |
| ttc atg att tcc tgg aga aac cca ggt gtt gct caa gct caa att gat | 864 |
| tta gat gat tat gtt gtt gat ggt gtc att gct gct ttg gat ggt gtt | 912 |
| gaa gcc gct act ggt gaa aga gaa gtt cac ggt att ggt tac tgt att | 960 |
| ggt ggt acc gct ttg tct tta gct atg ggt tgg ttg gcc gcc aga aga | 1008 |
| caa aaa caa aga gtt aga act gct act ttg ttt act act ttg ttg gat | 1056 |
| ttc tcc caa cca ggt gaa ttg ggt att ttt att cat gaa cca att atc | 1104 |
| gcc gcc tta gaa gcc caa aat gaa gct aaa ggt att atg gat ggt aga | 1152 |
| caa ttg gcc gtc tcc ttc tct ttg ttg aga gaa aac tct tta tat tgg | 1200 |
| aat tac tat att gat tct tac tta aaa ggt caa tct cca gtt gct ttt | 1248 |
| gat ttg ttg cac tgg aac tct gat tct act aat gtt gcc ggt aaa act | 1296 |
| cat aac tct ttg ttg aga aga tta tat ttg gaa aat caa ttg gtt aaa | 1344 |
| ggt gaa tta aaa att aga aac act aga att gat tta ggt aaa gtt aaa | 1392 |
| act cca gtt ttg ttg gtt tct gcc gtt gat gat cac att gct tta tgg | 1440 |
| caa ggt acc tgg caa ggt atg aaa ttg ttc ggt ggt gaa caa aga ttt | 1488 |
| tta ttg gcc gaa tcc ggt cat att gct ggt att att aat cca cca gct | 1536 |
| gct aac aaa tac ggt ttc tgg cac aat ggt gct gaa gct gaa tct cca | 1584 |
| gaa tct tgg ttg gct ggt gcc acc cat caa ggt ggt tcc tgg tgg cca | 1632 |
| gaa atg atg ggt ttt att caa aac aga gat gaa ggt tct gaa cca gtc | 1680 |
| cca gcc aga gtc cca gaa gaa ggt ttg gct cca gct cca ggt cac tat | 1728 |
| gtc aaa gtt aga tta aac cca gtt ttc gct tgt cca acc gaa gaa gat | 1776 |
| gct gct taa | 1785 |

<210> SEQ ID NO 6
<211> LENGTH: 405
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(405)

<400> SEQUENCE: 6

| | |
|---|---|
| atg tct gct caa tcc ttg gaa gtt ggt caa aaa gct aga tta tct aaa | 48 |
| aga ttc ggt gcc gcc gaa gtt gct gct ttt gct gcc tta tct gaa gat | 96 |

```
ttc aac cca ttg cac ttg gat cca gct ttt gct gct act acc gcc ttc      144 gaa aga cca atc gtc cat ggt atg ttg tta gct tct tta ttt tcc ggt      192 ttg ttg ggt caa caa ttg cca ggt aaa ggt tct att tat ttg ggt caa      240 tct tta tct ttc aaa ttg cca gtc ttt gtc ggt gat gaa gtt acc gct      288 gaa gtt gaa gtt act gct ttg aga gaa gat aaa cca att gct act ttg      336 act act aga att ttc act caa ggt ggt gct tta gct gtt acc ggt gaa      384 gct gtt gtc aaa ttg cca taa                                          405
```

<210> SEQ ID NO 7
<211> LENGTH: 1794
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(1794)

<400> SEQUENCE: 7

```
atg tct caa cca tct tat ggt cca ttg ttc gaa gct ttg gct cat tac       48 aat gat aaa ttg ttg gct atg gct aaa gct caa acc gaa aga act gct       96 caa gcc ttg ttg caa act aac ttg gat gat ttg ggt caa gtt ttg gaa      144 caa ggt tct caa caa cca tgg caa ttg att caa gct caa atg aat tgg      192 tgg caa gat caa tta aaa ttg atg caa cac act ttg tta aaa tct gct      240 ggt caa cca tct gaa cca gtt att act cca gaa aga tct gat aga aga      288 ttt aaa gct gaa gct tgg tct gaa caa cca att tat gat tac tta aaa      336 caa tcc tat ttg tta act gct aga cat ttg ttg gct tct gtt gat gct      384 ttg gaa ggt gtc cca caa aaa tct aga gaa aga ttg aga ttc ttt act      432 aga caa tac gtc aac gct atg gct cca tct aat ttc ttg gct act aac      480 cca gaa ttg tta aaa ttg act ttg gaa tcc gat ggt caa aat ttg gtt      528 aga ggt ttg gct tta ttg gct gaa gat ttg gaa aga tct gct gat caa      576 tta aac att aga ttg act gat gaa tcc gct ttt gaa tta ggt aga gat      624 ttg gct ttg act cca ggt aga gtt gtt caa aga act gaa tta tat gaa      672 tta att caa tac tct cca act act gaa acc gtt ggt aaa acc cca gtt      720 ttg atc gtt cca cca ttc att aat aaa tat tac att atg gat atg aga      768 cca caa aac tcc ttg gtc gct tgg ttg gtc gct caa ggt caa acc gtt      816 ttc atg att tcc tgg aga aac cca ggt gtt gct caa gct caa att gat      864 tta gat gat tat gtt gtt gat ggt gtc att gct gct ttg gat ggt gtt      912 gaa gcc gct act ggt gaa aga gaa gtt cac ggt att ggt tac tgt att      960 ggt ggt acc gct ttg tct tta gct atg ggt tgg ttg gcc gcc aga aga     1008 caa aaa caa aga gtt aga act gct act ttg ttt act act ttg ttg gat     1056 ttc tcc caa cca ggt gaa ttg ggt att ttt att cat gaa cca att atc     1104 gcc gcc tta gaa gcc caa aat gaa gct aaa ggt att atg gat ggt aga     1152 caa ttg gcc gtc tcc ttc tct ttg ttg aga gaa aac tct tta tat tgg     1200 aat tac tat att gat tct tac tta aaa ggt caa tct cca gtt gct ttt     1248
```

-continued

```
gat ttg ttg cac tgg aac tct gat tct act aat gtt gcc ggt aaa act      1296
cat aac tct ttg ttg aga aga tta tat ttg gaa aat caa ttg gtt aaa      1344
ggt gaa tta aaa att aga aac act aga att gat tta ggt aaa gtt aaa      1392
act cca gtt ttg tgt gtt tct gcc gtt gat gat cac att gct tta tgg      1440
caa ggt acc tgg caa ggt atg aaa ttg ttc ggt ggt gaa caa aga ttt      1488
tta ttg gcc gaa tcc ggt cat att gct ggt att att aat cca cca gct      1536
gct aac aaa tac ggt ttc tgg cac aat ggt gct gaa gct gaa tct cca      1584
gaa tct tgg ttg gct ggt gcc acc cat caa ggt ggt tcc tgg tgg cca      1632
gaa atg atg ggt ttt att caa aac aga gat gaa ggt tct gaa cca gtc      1680
cca gcc aga gtc cca gaa gaa ggt ttg gct cca gct cca ggt cac tat      1728
gtc aaa gtt aga tta aac cca gtt ttc gct tgt cca acc gaa gaa gat      1776
gct gct tct aaa ttg taa                                              1794
```

<210> SEQ ID NO 8
<211> LENGTH: 1794
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(1794)

<400> SEQUENCE: 8

```
atg tct caa cca tct tat ggt cca ttg ttc gaa gct ttg gct cat tac        48
aat gat aaa ttg gct atg gct aaa gct caa acc gaa aga act gct            96
caa gcc ttg ttg caa act aac ttg gat gat ttg ggt caa gtt ttg gaa       144
caa ggt tct caa caa cca tgg caa ttg att caa gct caa atg aat tgg       192
tgg caa gat caa tta aaa ttg atg caa cac act ttg tta aaa tct gct       240
ggt caa cca tct gaa cca gtt att act cca gaa aga tct gat aga aga       288
ttt aaa gct gaa gct tgg tct gaa caa cca att tat gat tac tta aaa       336
caa tcc tat ttg tta act gct aga cat ttg gtt gct tct gtt gat gct       384
ttg gaa ggt gtc cca caa aaa tct aga gaa aga ttg aga ttc ttt act       432
aga caa tac gtc aac gct atg gct cca tct aat ttc ttg gct act aac       480
cca gaa ttg tta aaa ttg act ttg gaa tcc gat ggt caa aat ttg gtt       528
aga ggt ttg gct tta ttg gct gaa gat ttg gaa aga tct gct gat caa       576
tta aac att aga ttg act gat gaa tcc gct ttt gaa tta ggt aga gat       624
ttg gct ttg act cca ggt aga gtt gtt caa aga act gaa tta tat gaa       672
tta att caa tac tct cca act act gaa acc gtt ggt aaa acc cca gtt       720
ttg atc gtt cca cca ttc att aat aaa tat tac att atg gat atg aga       768
cca caa aac tcc ttg gtc gct tgg ttg gtc gct caa ggt caa acc gtt       816
ttc atg att tcc tgg aga aac cca ggt gtt gct caa gct caa att gat       864
tta gat gat tat gtt gtt gat ggt gtc att gct gct ttg gat ggt gtt       912
gaa gcc gct act ggt gaa aga gaa gtt cac ggt att ggt tac tgt att       960
ggt ggt acc gct ttg tct tta gct atg ggt tgg ttg gcc gcc aga aga      1008
```

```
caa aaa caa aga gtt aga act gct act ttg ttt act act ttg ttg gat    1056
ttc tcc caa cca ggt gaa ttg ggt att ttt att cat gaa cca att atc    1104
gcc gcc tta gaa gcc caa aat gaa gct aaa ggt att atg gat ggt aga    1152
caa ttg gcc gtc tcc ttc tct ttg ttg aga gaa aac tct tta tat tgg    1200
aat tac tat att gat tct tac tta aaa ggt caa tct cca gtt gct ttt    1248
gat ttg ttg cac tgg aac tct gat tct act aat gtt gcc ggt aaa act    1296
cat aac tct ttg ttg aga aga tta tat ttg gaa aat caa ttg gtt aaa    1344
ggt gaa tta aaa att aga aac act aga att gat tta ggt aaa gtt aaa    1392
act cca gtt ttg ttg gtt tct gcc gtt gat gat cac att gct tta tgg    1440
caa ggt acc tgg caa ggt atg aaa ttg ttc ggt ggt gaa caa aga ttt    1488
tta ttg gcc gaa tcc ggt cat att gct ggt att att aat cca cca gct    1536
gct aac aaa tac ggt ttc tgg cac aat ggt gct gaa gct gaa tct cca    1584
gaa tct tgg ttg gct ggt gcc acc cat caa ggt ggt tcc tgg tgg cca    1632
gaa atg atg ggt ttt att caa aac aga gat gaa ggt tct gaa cca gtc    1680
cca gcc aga gtc cca gaa gaa ggt ttg gct cca gct cca ggt cac tat    1728
gtc aaa gtt aga tta aac cca gtt ttc gct tgt cca acc gaa gaa gat    1776
gct gct gct aaa att taa                                            1794
```

<210> SEQ ID NO 9
<211> LENGTH: 414
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(414)

<400> SEQUENCE: 9

```
atg tct gct caa tcc ttg gaa gtt ggt caa aaa gct aga tta tct aaa    48
aga ttc ggt gcc gcc gaa gtt gct gct ttt gct gcc tta tct gaa gat    96
ttc aac cca ttg cac ttg gat cca gct ttt gct gct act acc gcc ttc    144
gaa aga cca atc gtc cat ggt atg ttg tta gct tct tta ttt tcc ggt    192
ttg ttg ggt caa caa ttg cca ggt aaa ggt tct att tat ttg ggt caa    240
tct tta tct ttc aaa ttg cca gtc ttt gtc ggt gat gaa gtt acc gct    288
gaa gtt gaa gtt act gct ttg aga gaa gat aaa cca att gct act ttg    336
act act aga att ttc act caa ggt ggt gct tta gct gtt acc ggt gaa    384
gct gtt gtc aaa ttg cca tct aaa ttg taa                            414
```

<210> SEQ ID NO 10
<211> LENGTH: 414
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(414)

<400> SEQUENCE: 10

| | |
|---|---|
| atg tct gct caa tcc ttg gaa gtt ggt caa aaa gct aga tta tct aaa | 48 |
| aga ttc ggt gcc gcc gaa gtt gct gct ttt gct gcc tta tct gaa gat | 96 |
| ttc aac cca ttg cac ttg gat cca gct ttt gct gct act acc gcc ttc | 144 |
| gaa aga cca atc gtc cat ggt atg ttg tta gct tct tta ttt tcc ggt | 192 |
| ttg ttg ggt caa caa ttg cca ggt aaa ggt tct att tat ttg ggt caa | 240 |
| tct tta tct ttc aaa ttg cca gtc ttt gtc ggt gat gaa gtt acc gct | 288 |
| gaa gtt gaa gtt act gct ttg aga gaa gat aaa cca att gct act ttg | 336 |
| act act aga att ttc act caa ggt ggt gct tta gct gtt acc ggt gaa | 384 |
| gct gtt gtc aaa ttg cca gct aaa att taa | 414 |

<210> SEQ ID NO 11
<211> LENGTH: 74
<212> TYPE: DNA
<213> ORGANISM: Artificial Sequence
<220> FEATURE:
<223> OTHER INFORMATION: Synthetic Primer

<400> SEQUENCE: 11

| | |
|---|---|
| aattgattta gatgattatg ttgttgatgg tgtcattgct gctttggatg gtgttgaagc | 60 |
| cgctactggt gaaa | 74 |

<210> SEQ ID NO 12
<211> LENGTH: 44
<212> TYPE: DNA
<213> ORGANISM: Artificial Sequence
<220> FEATURE:
<223> OTHER INFORMATION: Synthetic Primer

<400> SEQUENCE: 12

| | |
|---|---|
| atggtactgc agttacaatt tagaagcagc atcttcttcg gttg | 44 |

<210> SEQ ID NO 13
<211> LENGTH: 44
<212> TYPE: DNA
<213> ORGANISM: Artificial Sequence
<220> FEATURE:
<223> OTHER INFORMATION: Synthetic Primer

<400> SEQUENCE: 13

| | |
|---|---|
| atggtactgc agttaaattt tagcagcagc atcttcttcg gttg | 44 |

<210> SEQ ID NO 14
<211> LENGTH: 82
<212> TYPE: DNA
<213> ORGANISM: Artificial Sequence
<220> FEATURE:
<223> OTHER INFORMATION: Synthetic Primer

<400> SEQUENCE: 14

| | |
|---|---|
| ttttcatatg tctgctcaat ccttggaagt tggtcaaaaa gctagattat ctaaagatt | 60 |
| cggtgccgcc gaagttgctg ct | 82 |

<210> SEQ ID NO 15
<211> LENGTH: 44
<212> TYPE: DNA
<213> ORGANISM: Artificial Sequence
<220> FEATURE:
<223> OTHER INFORMATION: Synthetic Primer

```
<400> SEQUENCE: 15
atggtactgc agttacaatt tagatggcaa tttgacaaca gctt                      44

<210> SEQ ID NO 16
<211> LENGTH: 44
<212> TYPE: DNA
<213> ORGANISM: Artificial Sequence
<220> FEATURE:
<223> OTHER INFORMATION: Synthetic Primer

<400> SEQUENCE: 16
atggtactgc agttaaattt tagctggcaa tttgacaaca gctt                      44

<210> SEQ ID NO 17
<211> LENGTH: 1017
<212> TYPE: DNA
<213> ORGANISM: Candida maltosa
<220> FEATURE:
<223> OTHER INFORMATION: ALK1 promoter

<400> SEQUENCE: 17
atgcatgaac aggatttaat cccaagaaaa aagtctattt tctattttca caaggaaact      60
ggaaaaacct ttttgtgttt tgaagtagct ccgtaataac ctgtaaaaaa ataaattttg     120
aagatttgac ttgctgatga aaatgctatc agtgtagctc tagacttgat actagactat     180
gatggcaaca catggtggtc aacgtgcaag acatcaccca atgagaagac tgctaaccag     240
aaaaaaaagg ggacaaaaga aaaactcgag agaaaaagtc aaattggtgt aaaattggct     300
atttttggta ctttcctaat ggggaaatta attgttttaaa attccagtttt ttccagagtt   360
aagatttcga ccaattattt ttaatccata tgatcttcat cattatcaac ttgtgaaaaa     420
taataatcga ggtacgttta atacgagata ttagtctacg gctatgaatg ttggatatac     480
ttcattgacg atcagaagct tgattggtta ttcaggtgca tgtgtggata taaacccaac     540
aaattatcta gcaactgtgc cttccccaca ttggtcaaag aaaccctaaa gcaaattaaa     600
atctggataa ataaatcatt catttcacat tttccggtta gtataaggtt ttttaaattt     660
tttttttacag tttagccctt tcaattacca aatacggtaa caatgtgctt tgtaacatgc    720
agggatttt ctccgttgct gttttctcca catgctttta atgtgtaata aattaaaaaa     780
attacaaaga aaaaccggca tataagcatc ggagtttaca ttgttaacta actgcaaaat     840
ggcgatgttt caaatcaaca aaatttaaaa aaacccccaaa aaaaaagtat catataaatt   900
aaactcaaaa tccttttgat tgcataaaat ttttaaatct cttcttttt ttcttttta     960
ctttcttatc tattctattc tttttttata tatctaattc atttataaca tctggtc      1017

<210> SEQ ID NO 18
<211> LENGTH: 750
<212> TYPE: DNA
<213> ORGANISM: Candida maltosa
<220> FEATURE:
<223> OTHER INFORMATION: ALK5 Promoter

<400> SEQUENCE: 18
aagcttcaca tggatcaatt gcgtttgtca catgtggtca tccagctatg gttgatgagg      60
ttagatattt tacttgtaag aatattaaca acccagaaaa gaaagagtt gatttctttg     120
aacaagtgca agtctgggct tagacgttta ttttgtttt tgttgagtgg taatacatat      180
tcttcgtatc tatgaagatt tttcacacgc ggatagtaat tgtactagcc gcttctttaa     240
gtaactgatt tacccaacaa gtacatggta atacaaactc tcactcacta gacttcgctt     300
```

```
ctagttgctt caaattagac ggttataatg tatgccaagg ttttgtgtaa tttcacggtg    360
attaaccttt tcccctttt atactcctca ttatccacga tgtaatctga tctatgaacg     420
tgataagtaa cattacttag tcattaagta tggccaattc agttatacat attagtaatg    480
ctccacatcc attgtattca tatgtaatgc caaatatcac attcatttac acagaatcgg    540
ttttgttaaa tactccgcta ttgtacagca caataggat tatgtacaga atgaaaaaca    600
aaaggcggag aaattcgacg gaaaaattta ttatttacaa atcgtattcc cgcattatct    660
ataaaacaga ttcaaaataa tctagatctc tttttttgc ttcctttat ttctttttaa     720 ataagattaa actaaaaata tgattgatga                                    750

<210> SEQ ID NO 19
<211> LENGTH: 444
<212> TYPE: DNA
<213> ORGANISM: Candida maltosa
<220> FEATURE:
<223> OTHER INFORMATION: POX2 Promoter

<400> SEQUENCE: 19
atcaatagat agagggaact acaattgttc tatttctctt ggaagtcgct ttttttaaca    60
gatagttgtg caaacttttg ttttgaaaag tagtgcaaag acgaaaaatt cgcacaaaaa    120 ttcctaatt gggccaaact tctatggggg acagtccgga atgaggaaaa tgcacttata     180 ctttttttt tcatccaca agaaaaaaa aaggcggggc agctgaaaat gaaaaaaagc     240
gggtttctat acacaaccgt ggggatgaaa attcaagcat caacaatagc tagtttaata    300
tttaaaaata ctgatatccc ccttataaat aacttttgat tcaatttctt ttcttcttct    360 tcttttttt ttattttca gtctccata cttttctct tttttttta tatttatttc       420 ttatttatct atacttaact cacc                                          444

<210> SEQ ID NO 20
<211> LENGTH: 218
<212> TYPE: DNA
<213> ORGANISM: Candida maltosa
<220> FEATURE:
<223> OTHER INFORMATION: ALK1 Terminator

<400> SEQUENCE: 20
atagatggat ttttcttttt tatgtgtatt tccggttaat aaatgtttaa attttttttt    60
taataaaaat atttgtagtt atttatatgc aaaaaaaaaa aatattcaaa gcaatcttcc    120
tttctttctt tatctttccc ccatgctaag gtctaaaaca ccacaactta aaacccaact    180
taaccgtata atactaagat caatctccaa agatgcat                           218

<210> SEQ ID NO 21
<211> LENGTH: 46
<212> TYPE: DNA
<213> ORGANISM: Artificial Sequence
<220> FEATURE:
<223> OTHER INFORMATION: Synthetic Primer

<400> SEQUENCE: 21
tttttcagct ggagctcgtc gacatgcatg aacaggattt aatccc                  46

<210> SEQ ID NO 22
<211> LENGTH: 40
<212> TYPE: DNA
<213> ORGANISM: Artificial Sequence
<220> FEATURE:
<223> OTHER INFORMATION: Synthetic Primer
```

<400> SEQUENCE: 22
ccggaatcca tatgaccaga tgttataaat gaattagata                40

<210> SEQ ID NO 23
<211> LENGTH: 49
<212> TYPE: DNA
<213> ORGANISM: Artificial Sequence
<220> FEATURE:
<223> OTHER INFORMATION: Synthetic Primer

<400> SEQUENCE: 23
tttttcagct gctcgaggtc gacatgcatc acatggatca attgcgttt        49

<210> SEQ ID NO 24
<211> LENGTH: 35
<212> TYPE: DNA
<213> ORGANISM: Artificial Sequence
<220> FEATURE:
<223> OTHER INFORMATION: Synthetic Primer

<400> SEQUENCE: 24
ccggaattcc atatgtttag tttaatctta tttaa                35

<210> SEQ ID NO 25
<211> LENGTH: 43
<212> TYPE: DNA
<213> ORGANISM: Artificial Sequence
<220> FEATURE:
<223> OTHER INFORMATION: Synthetic Primer

<400> SEQUENCE: 25 tttttcccggg gtcgacatgc atatcaatag atagagggaa cta          43

<210> SEQ ID NO 26
<211> LENGTH: 31
<212> TYPE: DNA
<213> ORGANISM: Artificial Sequence
<220> FEATURE:
<223> OTHER INFORMATION: Synthetic Primer

<400> SEQUENCE: 26
tttttcatat ggtgagttaa gtatagataa a                    31

<210> SEQ ID NO 27
<211> LENGTH: 32
<212> TYPE: DNA
<213> ORGANISM: Artificial Sequence
<220> FEATURE:
<223> OTHER INFORMATION: Synthetic Primer

<400> SEQUENCE: 27
cggaagctta tagatggatt tttcttttt at                   32

<210> SEQ ID NO 28
<211> LENGTH: 46
<212> TYPE: DNA
<213> ORGANISM: Artificial Sequence
<220> FEATURE:
<223> OTHER INFORMATION: Synthetic Primer

<400> SEQUENCE: 28
tttttgatat cgagctcgtc gacatgcatc tttggagatt gatctt        46

<210> SEQ ID NO 29
<211> LENGTH: 1820
<212> TYPE: DNA
<213> ORGANISM: Candida maltosa
<220> FEATURE:
<221> NAME/KEY: CDS
<222> LOCATION: (538)..(1413)

<400> SEQUENCE: 29

```
gatccccttc ttcaaacctt taaatgacat tgtttcgttt ctctatgttt ggtatcggtt      60
cttcttcttc ttcaaaaaaa aggggggcac tattcaaaaa aaatattat aacagtatga     120 ttttttttccc tctcccgtcg attgaggttt ttttttttctc tttcgtcttg gtcttttgct    180
tttcactcca aaaatggaaa cacgcgcggc tcaactcgaa atccgtgatc aaaaaaataa    240
aggctgtgag tttcgagcca ataattatga attagtggta ttttttttaa agataaataa    300
tcaagaatcg cattagggag acgaaatatgc gttattcaaa taaaaagaca attcttttag    360
ggtagcattt cccttcaagt tcatcccaca tgtacattaa tgtcaatgat gtcgcagaag    420
ttaaattagc agaagaaaaa aaaaatgtga attactccga gtcaactctt ctttctcttc    480 ttcttttttct tctttatcac cataatcacc accaccacca ccaccaccag ctcccag      537 atg act tca act aac tta gaa gga act ttc cca ttg att gcc aaa ggt      585 aaa gtc aga gat att tac caa gtt gac gac aac act ctt tta ttc gtt      633 gct act gat aga att tcc gca tac gat gtg att atg tct aat ggt atc      681 cca aat aaa ggt aaa atc tta acc aaa ttg tct gaa ttc tgg ttt gat      729 ttc ttg cca att gaa aac cat tta atc aaa gga gac att ttc caa aaa      777 tat cct caa cta gaa cca tat aga aac caa ttg gaa ggc aga tcc tta      825 ctt gtt aga aaa ttg aaa ttg atc cct ctt gaa gtt att gtt aga ggt      873 tac atc acc ggt tcc ggc tgg aaa gaa tac caa aaa tct aaa acc gtc      921 cac ggt att cct att ggt gat gtg gtt gaa tca caa caa atc act cct      969 atc ttc acc cca tcc act aaa gca gaa caa ggt gaa cat gat gaa aat     1017 atc acc aaa gaa caa gct gac aag att gtt gga aaa gaa tta tgt gat     1065 aga att gaa aaa att gct att gat ttg tac acc aaa gcc aga gat tac     1113 gct gcc act aaa gga att att atc gct gat act aaa ttt gaa ttt ggt     1161 tta gat ggt gac aac atc gtt ctt gtt gac gaa gtt tta act cca gat     1209 tct tcc aga ttc tgg aat gct gct aaa tac gaa gtt ggt aaa tct caa     1257 gac tct tac gat aaa caa ttt ttg aga gat tgg tta act tct aat ggt     1305 gtt gct ggt aaa gat ggt gtt gct atg cct gaa gac att gtc act gaa     1353 acc aag agc aaa tac gtt gaa gct tac gaa aat tta act ggt gac aaa     1401 tgg caa gaa taa attaaggata tctattatta aagctttcta tttatcccaa         1453
actttcgtag tattttctga catgttcaga tgttttact ttatctttcc tgaaattttt     1513
gatttctaac cgactcttgc atgtagctct tgataatgca acatatgctt gaccattagc    1573
aaaacttcta cctaaatcta ttttgactct gtccaaagtt tgaccttgag ctttgtggat    1633
cgacatcgcc cacgcaaaga tcatttggtt tgttttatg gtgggttatt ggcacttggt    1693
gcaactgatg gtttaacttt ggaagaggct aagaaattga agacttggaa tgaagaacgt   1753
```

```
gcatctgatt tcaaattggg tgaagaattg acttatactt gttataaaat gtatcatgat    1813
gttgatc                                                              1820
```